(12) United States Patent
Miller et al.

(10) Patent No.: US 7,648,984 B2
(45) Date of Patent: Jan. 19, 2010

(54) ANTIBACTERIAL AGENTS

(75) Inventors: William Henry Miller, Collegeville, PA (US); Jeffrey Michael Axten, Collegeville, PA (US); Mark Andrew Seefeld, Collegeville, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 440 days.

(21) Appl. No.: 11/570,600

(22) PCT Filed: Jul. 13, 2005

(86) PCT No.: PCT/US2005/024801

§ 371 (c)(1),
(2), (4) Date: Dec. 14, 2006

(87) PCT Pub. No.: WO2006/017326

PCT Pub. Date: Feb. 16, 2006

(65) Prior Publication Data

US 2007/0203127 A1    Aug. 30, 2007

Related U.S. Application Data

(60) Provisional application No. 60/587,439, filed on Jul. 13, 2004.

(51) Int. Cl.
*A61K 31/542* (2006.01)

(52) U.S. Cl. .................. 514/227.5; 514/230.5; 514/300; 514/422; 514/456; 544/58.2; 544/58.6; 544/105; 546/122; 548/518; 549/396

(58) Field of Classification Search .................. 546/122
See application file for complete search history.

(56) References Cited

U.S. PATENT DOCUMENTS 6,440,995 B1    8/2002    Alanine et al. .............. 514/312

OTHER PUBLICATIONS

Yoneyama et al. "Antibiotic Resistance in Bacteria and Its Future for Novel Antibiotic Development", 2006, Bioscience, Biotechnology and Biochemistry, 70, 1060-1075.*

* cited by examiner

*Primary Examiner*—James O Wilson
*Assistant Examiner*—Brian McDowell
(74) *Attorney, Agent, or Firm*—Reid S. Willis; John Lernanowicz

(57) ABSTRACT

Naphthalene, quinoline, quinoxaline and naphthyridine derivatives useful in the treatment of bacterial infections in mammals, particularly humans, are disclosed herein.

10 Claims, No Drawings

ANTIBACTERIAL AGENTS

This is a 371 of International Application No. PCT/US2005/02801, filed 13 Jul. 2005, which claims benefit of U.S. Provisional Application No. 60/587,439, filed 13 Jul. 2004.

FIELD OF THE INVENTION

This invention relates to novel compounds, compositions containing them, their use as antibacterials, and processes for their preparation.

BACKGROUND OF THE INVENTION

The emergence of pathogens resistant to known antibiotic therapy is becoming a serious global healthcare problem (Chu, et al., (1996) *J. Med. Chem.*, 39: 3853-3874). Thus, there is a need to discover new broad spectrum antibiotics useful in combating multidrug-resistant organisms. Importantly, it has now been discovered that certain compounds have antibacterial activity, and, therefore, may be useful for the treatment of bacterial infections in mammals, particularly in humans.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also processes for the preparation of compounds of formula (I), as well as processes for the preparation of intermediates useful in the synthesis of compounds of formula (I). This invention is also a method of treating bacterial infections in mammals, particularly in humans.

DETAILED DESCRIPTION OF THE INVENTION

This invention provides a compound of formula (I) or a pharmaceutically acceptable salt, solvate or derivative thereof:

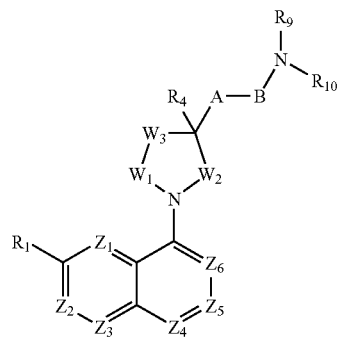

(I)

wherein:

$Z_1$, $Z_3$, and $Z_4$ are independently N or $CR^{1a}$;
$Z_2$, $Z_5$, and $Z_6$ are each $CR^{1a}$;
$R_1$ and $R^{1a}$ are independently at each occurrence hydrogen; cyano; halogen; hydroxy; $(C_{1-6})$alkoxy unsubstituted or substituted by $(C_{1-6})$alkoxy, hydroxy, amino, piperidyl, guanidino or amidino any of which is unsubstitued or N-substituted by one or two $(C_{1-6})$alkyl, acyl, $(C_{1-6})$alkylsulphonyl, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide; or an amino, piperidyl, guanidino or amidino group unsubstituted or N-substituted by one or two $(C_{1-6})$alkyl, acyl or $(C_{1-6})$alkylsulphonyl groups; or $R_1$ and $R^{1a}$ of $Z_2$ together form ethylenedioxy;

$W_1$, $W_2$, and $W_3$ are each $CR_2R_3$;
A is O; $NR_5$; $S(O)_n$; or $NR_6(C=O)$;
B is $(CR_7R_8)_{n'}$;
$R_2$, $R_3$, $R_4$, $R_7$, and $R_8$ are independently hydrogen; thiol; $(C_{1-6})$alkylthio; halogen; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenylcarbonyl; $(C_{2-6})$alkenyloxycarbonyl; aralkyl; aryl; heterocyclyl; heterocyclylalkyl; hydroxy; amino; $NR^{1b}R^{1b'}$; $(C_{1-6})$alkylsulphonyl; $(C_{2-6})$alkenylsulphonyl; or $(C_{1-6})$aminosulphonyl wherein the amino group is optionally and independently substituted by hydrogen, $(C_{1-6})$alkyl, $(C_{2-6})$alkenyl or aralkyl;

$R_5$, $R_6$ and $R_9$ are independently hydrogen, trifluoromethyl; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; aryl; aralkyl; $(C_{3-8})$cycloalkyl; heterocyclyl; or heterocyclylalkyl;
n is 0, 1, or 2;
n' is 1 or 2;
$R^{1b}$ and $R^{1b'}$ are independently at each occurrence hydrogen; $(C_{1-6})$alkyl; aralkyl; aryl; heterocyclyl; heterocyclylalkyl; or together with the nitrogen that they are attached forn an aziridine, azetidine, pyrrolidine, piperidine or hexamethyleneimine ring (wherein said aziridine, azetidine, pyrrolidine, piperidine or hexamethyleneimine ring are optionally substiuted with from 1 to 3 substituents selected from halogen, hydroxy; cyano; nitro; $(C_{1-6})$alkyl; and aryl);
$R_{10}$ is $UR_{11}$;
U is $CH_2$; $C(=O)$; or $SO_2$;
$R_{11}$ is a substituted or unsubstituted bicyclic carbocyclic or heterocyclic ring system (A):

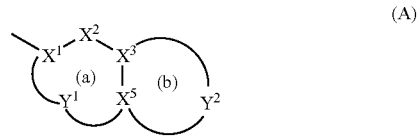

(A)

containing up to four heteroatoms in each ring in which at least one of rings (a) and (b) is aromatic;

$X^1$ is C or N when part of an aromatic ring or $CR_{12}$ when part of a non aromatic ring;

$X^2$ is N, $NR_{13}$, O, $S(O)_{n''}$, CO or $CR_{12}$ when part of an aromatic or non-aromatic ring or may in addition be $CR_{14}R_{15}$ when part of a non aromatic ring;

n" is independently at each occurrence 0, 1 or 2;

$X^3$ and $X^5$ are independently N or C;

$Y^1$ is a 0 to 4 atom linker group each atom of which is independently selected from N, $NR_{13}$, O, $S(O)_{n''}$, CO and $CR_{12}$ when part of an aromatic or non-aromatic ring or may additionally be $CR_{14}R_{15}$ when part of a non aromatic ring, $Y^2$ is a 2 to 6 atom linker group, each atom of $Y^2$ being independently selected from N, $NR_{13}$, O, $S(O)_{n''}$, CO and $CR_{12}$ when part of an aromatic or non-aromatic ring or may additionally be $CR_{14}R_{15}$ when part of a non aromatic ring;

$R_{12}$, $R_{14}$ and $R_{15}$ are at each occurrence independently selected from: H; $(C_{1-4})$alkylthio; halo; $(C_{1-4})$alkyl; $(C_{2-4})$alkenyl; hydroxy; hydroxy$(C_{1-4})$alkyl; mercapto$(C_{1-4})$alkyl; $(C_{1-4})$alkoxy; trifluoromethoxy; nitro; cyano; carboxy; amino or aminocarbonyl unsubstituted or substituted by $(C_{1-4})$alkyl;

$R_{13}$ is at each occurrence independently hydrogen; trifluoromethyl; $(C_{1-4})$alkyl unsubstituted or substituted by hydroxy, carboxy, $(C_{1-4})$alkoxy, $(C_{1-6})$alkylthio, halo or trifluoromethyl; $(C_{2-4})$alkenyl; or aminocarbonyl wherein the amino group is optionally substituted with $(C_{1-4})$alkyl;

or a pharmaceutically acceptable salt or solvate thereof.

In some embodiments, this invention provides a compound of formula (I) wherein $Z_1$ and $Z_4$ are N and $Z_3$ is $CR^{1a}$.

In certain embodiments, this invention provides a compound of formula (I) wherein $R_1$ is $OCH_3$.

In some embodiments, this invention describes a compound of formula (I) wherein $R^{1a}$ is at each occurrence independently hydrogen; halogen; or cyano.

In some aspects, this invention describes a compound of formula (I) wherein A is O.

In certain aspects, this invention describes a compound of formula (I) wherein A is $S(O)_n$.

In some embodiments, this invention describes a compound of formula (I) wherein A is $NR_5$.

In certain embodiments, this invention describes a compound of formula (I) wherein A is $NR_6(C=O)$.

In some embodiments, this invention describes a compound of formula (I) wherein U is $C(=O)$.

In certain embodiments, this invention describes a compound of formula (I) wherein U is $SO_2$.

In some embodiments, this invention describes a compound of formula (I) wherein U is $CH_2$.

In certain embodiments, this invention describes a compound of formula (I) wherein $R_{11}$ is 4H-Pyrido[3,2-b][1,4]thiazin-3-oxo-6-yl; 2,3-Dihydro-benzo[1,4]dioxin-6-yl; 4H-Pyrido[3,2-b][1,4]oxazin-3-oxo-6-yl; or 2,3-Dihydro-[1,4]dioxino[2,3-c]-pyridin-6-yl.

In some embodiments, this invention describes a compound of formula (I) wherein $Z_1$ and $Z_4$ are N and $Z_3$ is $CR^{1a}$; $R_1$ is $OCH_3$; $R^{1a}$ is at each occurrence independently hydrogen; halogen; or cyano; A is $NR_5$; $R_5$ is hydrogen; $R_2$, $R_3$, $R_4$, $R_7$, and $R_8$ are independently hydrogen; halogen; $(C_{1-6})$alkyl; or hydroxy; or $NR^{1b}R^{1b'}$; and $R_9$ is hydrogen.

In certain embodiments, this invention describes a compound of formula (I) wherein $Z_1$ and $Z_4$ are N; $Z_3$ is $CR^{1a}$; $R_1$ is $OCH_3$; $R^{1a}$ is at each occurrence independently hydrogen; halogen; or cyano; A is $NR_5$; $R_5$ is hydrogen; $R_2$, $R_3$, $R_4$, $R_7$, and $R_8$ are independently hydrogen; halogen; $(C_{1-6})$alkyl; or hydroxy; or $NR^{1b}R^{1b'}$; $R_9$ is hydrogen; and $R_{11}$ is 4H-Pyrido[3,2-b][1,4]thiazin-3-oxo-6-yl; 2,3-Dihydro-benzo[1,4]dioxin-6-yl; 4H-Pyrido[3,2-b][1,4]oxazin-3-oxo-6-yl; or 2,3-Dihydro-[1,4]dioxino[2,3-c]-pyridin-6-yl.

In some embodiments, this invention describes a compound of formula (I) wherein $Z_1$ and $Z_4$ are N; $Z_3$ is $CR^{1a}$; $R_1$ is $OCH_3$; $R^{1a}$ is at each occurrence independently hydrogen; halogen; or cyano; A is $S(O)_n$; $R_2$, $R_3$, $R_4$, $R_7$, and $R_8$ are independently hydrogen; halogen; $(C_{1-6})$alkyl; or hydroxy; or $NR^{1b}R^{1b'}$; and $R_9$ is hydrogen.

In certain embodiments, this invention describes a compound of formula (I) wherein $Z_1$ and $Z_4$ are N; $Z_3$ is $CR^{1a}$; $R_1$ is $OCH_3$; $R^{1a}$ is at each occurrence independently hydrogen; halogen; or cyano; A is $S(O)_n$; $R_2$, $R_3$, $R_4$, $R_7$, and $R_8$ are independently hydrogen; halogen; $(C_{1-6})$alkyl; or hydroxy; or $NR^{1b}R^{1b'}$; $R_9$ is hydrogen; $R_{11}$ is 4H-Pyrido[3,2-b][1,4]thiazin-3-oxo-6-yl; 2,3-Dihydro-benzo[1,4]dioxin-6-yl; 4H-Pyrido[3,2-b][1,4]oxazin-3-oxo-6-yl; or 2,3-Dihydro-[1,4]dioxino[2,3-c]-pyridin-6-yl.

In some embodiments, this invention describes a compound of formula (I) wherein the compound is N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-sulfonamide; N-[2-({1-[6-(methyloxy)-1,5-naphthyridin-4-yl]-3-pyrrolidinyl}amino)ethyl]-3-oxo-3,4-dihydro-2H-pyrid6[3,2-b][1,4]thiazine-6-carboxamide; 6-({[2-({1-[6-(methyloxy)-1,5-naphthyridin-4-yl]-3-pyrrolidinyl}amino)ethyl]amino}methyl)-2H-pyrido[3,2-b][1,4]oxazin-3(4H)-one; 6-({[2-({1-[6-(methyloxy)-1,5-naphthyridin-4-yl]-3-pyrrolidinyl}amino)ethyl]amino}methyl)-2H-pyrido[3,2-b][1,4]thiazin-3(4H)-one; N-(2,3-dihydro[1,4]dioxino[2,3-c]pyridin-7-ylmethyl)-N'-{1-[6-(methyloxy)-1,5-naphthyridin-4-yl]-3-pyrrolidinyl}-1,2-ethanediamine; $N^1$-methyl-$N^1$-{1-[6-(methyloxy)-1,5-naphthyridin-4-yl]-3-pyrrolidinyl}-$N^2$-[(3-oxo-3,4-dihydro-2H-pyrido[3,2-b][1,4]oxazin-6-yl)methyl]glycinamide; 6-({[2-({1-[6-(methyloxy)-1,5-naphthyridin-4-yl]-3-pyrrolidinyl}thio)ethyl]amino}methyl)-2H-pyrido[3,2-b][1,4]oxazin-3(4H)-one; 6-({[2-({1-[6-(methyloxy)-1,5-naphthyridin-4-yl]-3-pyrrolidinyl}thio)ethyl]amino}methyl)-2H-pyrido[3,2-b][1,4]thiazin-3(4H)-one; (2,3-dihydro[1,4]dioxino[2,3-c]pyridin-7-ylmethyl)[2-({1-[6-(methyloxy)-1,5-naphthyridin-4-yl]-3-pyrrolidinyl}thio)ethyl]amine; N-[2-({1-[6-(methyloxy)-1,5-naphthyridin-4-yl]-3-pyrrolidinyl}thio)ethyl]-3-oxo-3,4-dihydro-2H-1,4-benzothiazine-6-sulfonamide; N-[2-({1-[6-(methyloxy)-1,5-naphthyridin-4-yl]-3-pyrrolidinyl}sulfonyl)ethyl]-3-oxo-3,4-dihydro-2H-1,4-benzothiazine-6-sulfonamide; N-[2-({1-[6-(methyloxy)-1,5-naphthyridin-4-yl]-3-pyrrolidinyl}thio)ethyl]-2,3-dihydro-1,4-benzodioxin-6-sulfonamide; or N-[2-({1-[6-(methyloxy)-1,5-naphthyridin-4-yl]-3-pyrrolidinyl}thio)ethyl]-3-oxo-3,4-dihydro-2H-pyrido[3,2-b][1,4]thiazine-6-carboxamide; or a pharmaceutically acceptable salt or solvate thereof.

In certain aspects, this invention describes a process for the preparation of a compound of formula (I), which process comprises:

(a) reacting a compound of formula (II) with a compound of formula (III) to give an intermediate having formula (IV);

(b) removing P wherein P is not hydrogen;

(c) reacting the product of step (b) with $L(U')R_{11}$, or $H(C=O)R_{11}$ (with subsequent reduction);

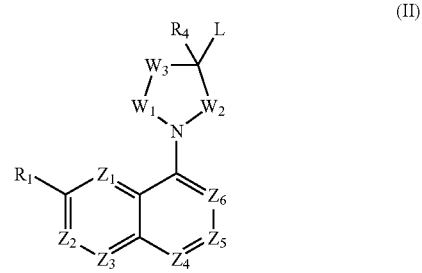

(II)

(III)

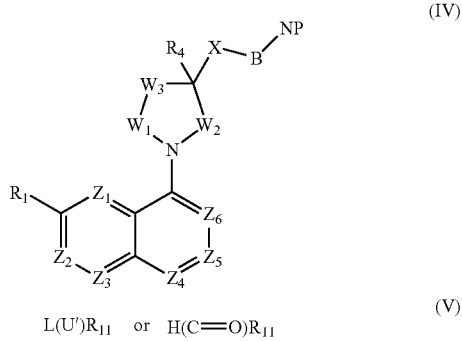

(IV)

L(U')R$_{11}$ or H(C=O)R$_{11}$ (V)

wherein:
Z$_1$, Z$_2$, Z$_3$, Z$_4$, Z$_5$, Z$_6$, W$_1$, W$_2$, W$_3$, B, and R$_{11}$ are as defined in claim 1;
X is NP or S;
P is hydrogen or a nitrogen protecting group;
U' is CH$_2$, SO$_2$, or C(=O);
R$_4$ is hydrogen; and
L is an independently selected leaving group.

In certain embodiments, this invention describes a pharmaceutical composition comprising a compound of formula I or any one of the embodiments described herein, and a pharmaceutically acceptable carrier.

In some embodiments, this invention describes a method of treating bacterial infections which comprises administering to a mammal in need thereof an effective amount of a compound of formula I or any of its embodiments described herein.

In some embodiments, this invention describes compounds of formula I wherein the (a) and (b) rings of R$_{11}$ are both aromatic as demonstrated by the following non-limiting examples: 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl.

In yet other embodiments, R$_{11}$ is defined by a non-aromatic (a) ring and aromatic (b) ring as illustrated by the following non-limiting examples: (2S)-2,3-dihydro-1 H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, 2,3-dihydro-benzo[1,4]dioxan-2-yl, 1-oxo-1,3,4,5-tetrahydrobenzo[c]azepin-2-yl.

In still other embodiments, R$_{11}$ is defined by an aromatic (a) ring and a non aromatic (b) ring as illustrated by the following non-limiting examples: 1,1,3-trioxo-1,2,3,4-tetrahydro-1/$^6$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydrobenzo[b][1,4]thiazepine-7-yl, 5-oxo-2,3-dihydro-5H-thiazolo[3,2-a]pyrimidin-6-yl, benzo[1,3]dioxol-5-yl, 2-oxo-2,3-dihydro-1H-pyrido[2,3-b][1,4]thiazin-7-yl, 2-oxo-2,3-dihydro-1H-pyrido[3,4-b][1,4]thiazin-7-yl, 3-oxo-3,4-dihydro-2H-pyrido[3,2-b][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl, 3,4-dihydro-2H-benzo[1,4]oxazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 3,4-dihydro-2H-pyrido[3,2-b][1,4]thiazin-6-yl.

Unless otherwise defined, the term "alkyl" when used alone or when forming part of other groups (such as the 'alkoxy' group) includes substituted or unsubstituted, straight or branched chain alkyl groups containing the specified range of carbon atoms. For example, the term "(C$_{1-6}$)alkyl" include methyl, ethyl, propyl, butyl, iso-propyl, sec-butyl, tert-butyl, iso-pentyl, and the like.

The term "alkenyl" means a substituted or unsubstituted alkyl group of the specified range of carbon atoms, wherein one carbon-carbon single bond is replaced by a carbon-carbon double bond. For example, the term "(C$_{2-6}$)alkenyl" include ethylene, 1-propene, 2-propene, 1-butene, 2-butene, and isobutene, and the like. Both cis and trans isomers are included.

The term "cycloalkyl" refers to subsituted or unsubstituted carbocyclic system of the specifed range of carbon atoms, which may contain up to two unsaturated carbon-carbon bonds. For example, the term "(C$_{3-7}$)cycloalkyl" include cyclopropyl, cyclobutyl, cyclopentyl, cyclopentenyl, cyclohexyl, cyclohexenyl, and cycloheptyl.

The term "alkoxy" refers to an O-alkyl radical where the alkyl group contains the specified range of carbon atoms and is as defined herein.

The term "acyl" refers to a C(=O)alkyl or a C(=O)aryl radical. In some embodiments, the alkyl group contains 13 or less carbons; in some embodiments 10 or less carbon atoms; in some embodiments 6 or less carbon atoms; and is as otherwise defined. Aryl is as defined herein.

The term "alkylcarbonyl" refers to a $(C_{1-6})$alkyl(C=O)$(C_{1-6})$alkyl group wherein alkyl is as otherwise defined herein.

The term "alkylsulphonyl" refers to a $SO_2$alkyl radical wherein the alkyl group contains the specified range of carbon atoms and is as defined herein.

The term "alkylthio" refers to a Salkyl wherein the alkyl group contains the specified range of carbon atoms and is as defined herein.

The term "aminosulphonyl" refers to a $SO_2N$ radical wherein the nitrogen is substituted as specified.

The term "aminocarbonyl" refers to a carboxamide radical wherein the nitrogen of the amide is substituted as defined.

The term "heterocyclylthio" refers to a S-heterocyclyl radical wherein the heterocyclyl moiety is as defined herein.

The term "heterocyclyloxy" refers to an O-heterocyclyl radical wherein heterocyclyl is as defined herein.

The term "arylthio" refers to an S-aryl radical wherein aryl is as defined herein.

The term "aryloxy" refers to an O-aryl radical wherein aryl is as defined herein.

The term "acylthio" refers to a S-acyl radical wherein acyl is as defined herein.

The term "acyloxy" refers to an O-acyl radical wherein acyl is as defined herein.

The term "alkoxycarbonyl" refers to a $CO_2$alkyl radical wherein the alkyl group contains the specified range of carbon atoms and is as defined herein.

The term "alkenyloxycarbonyl" refers to a $CO_2$alkyl radical wherein the alkenyl group contains the specified range of carbon atoms and is as defined herein.

The term "alkylsulphonyloxy" refers to an O—$SO_2$alkyl radical wherein the alkyl group contains the specified range of carbon atoms and is as defined herein.

The term "arylsulphonyl" refers to a $SO_2$aryl radical wherein aryl is as herein defined.

The term "arylsulphoxide" refers to a SOaryl radical wherein aryl is as defined herein.

Unless otherwise defined, suitable substituents for any alkyl, alkoxy, alkenyl, and cycloalkyl groups includes up to three substituents selected from the group consisting of hydroxy, halogen, nitro, cyano, carboxy, amino, amidino, sulphonamido, unsubstituted $(C_{1-3})$alkoxy, triflurometyl, and acyloxy.

Halo or halogen includes fluoro, chloro, bromo and iodo.

The term "haloalkyl" refers to an alkyl radical containing the specified range of carbon atoms and is as otherwise defined herein, which is further substituted with 1-3 halogen atoms.

The term "haloalkoxy" refers to an alkoxy radical of the specified range and as defined herein, which is further substituted with 1-3 halogen atoms.

The term "hydroxyalkyl" refers to an alkyl group as defined herein, further substituted with a hydroxy group.

Unless otherwise defined, the term "heterocyclic" or "heterocyclyl" as used herein includes optionally substituted aromatic and non-aromatic, single and fused, mono- or bicyclic rings suitably containing up to four hetero-atoms in each ring selected from oxygen, nitrogen and sulphur, which rings may be unsubstituted or C-substituted by, for example, up to three groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; hydroxy, $(C_{1-4})$alkyl; $(C_{1-4})$thioalkyl; $(C_{1-4})$alkoxy; nitro; cyano, carboxy; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl.

Each heterocyclic ring suitably has from 3 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include hydrogen; trifluoromethyl; $(C_{1-4})$alkyl optionally substituted by hydroxy, $(C_{1-4})$alkoxy, $(C_{1-4})$alkylthio, halo or trifluoromethyl; and $(C_{2-4})$alkenyl.

The term "heterocyclylalkyl" refers to a $(C_{1-6})$alkyl radical which bears as a substituent a heterocyclyl group, wherein heterocyclyl and alkyl are as herein defined. The heterocyclyl group may be joined to a primary, secondary or tertiary carbon of the $(C_{1-6})$alkyl chain.

When used herein the term "aryl", includes optionally substituted phenyl and naphthyl.

Aryl groups may be optionally substituted with up to five, preferably up to three, groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; $(C_{1-4})$hydroxyalkyl; $(C_{1-4})$alkylthio; $(C_{1-4})$alkoxy; nitro; cyano; carboxy; amino or aminocarbonyl optionally substituted by $(C_{1-4})$alkyl; $(C_{1-4})$alkylsulphonyl; $(C_{2-4})$alkenylsulphonyl.

The term "aralkyl" refers to a $(C_{1-6})$alkyl radical which bears as a substituent an aryl group, wherein aryl and alkyl are as herein defined. The aryl group may be joined to a primary, secondary or tertiary carbon of the $(C_{1-6})$alkyl chain.

This invention also contemplates that some of its structural embodiments may be present as a solvate. Solvates may be produced from crstallization from a given solvent or mixture of solvents, inorganic or organic. Solvates may also produced upon contact or exposure to solvent vapors, such as water. This invention includes within its scope stoichiometric and non-stoichiometric solvates including hydrates.

Furthermore, it will be understood that phrases such as "a compound of Formula I or a pharmaceutically acceptable salt, solvate or derivative thereof" are intended to encompass the compound of Formula I, a derivative of formula (I), a pharmaceutically acceptable salt of the compound of formula (I), a solvate of formula (I), or any pharmaceutically acceptable combination of these. Thus by way of non-limiting example used here for illustrative purpose, "a compound of Formula I or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable salts of the above-mentioned compounds of formula (I) include the free base form or their acid addition or quaternary ammonium salts, for example their salts with mineral acids e.g. hydrochloric, hydrobromic, sulphuric, nitric or phosphoric acids, or organic acids, e.g.

acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives. One of skill in the art will recognize that where compounds of the invention contain multiple basic sites, a compound of the invention maybe present as a salt complexed with more than one equivalent of a corresponding acid or mixture of acids.

Pharmaceutically acceptable derivatives refers to compounds of formula (I) that have been covalently modifed with a group that undergoes at least some in vivo cleavage to a compound of formula (I).

Examples of suitable pharmaceutically acceptable in vivo hydrolysable ester-forming groups include those forming esters which break down readily in the human body to leave the parent acid or its salt.

Suitable groups of this type include those of part formulae (i), (ii), (iii), (iv) and (v):

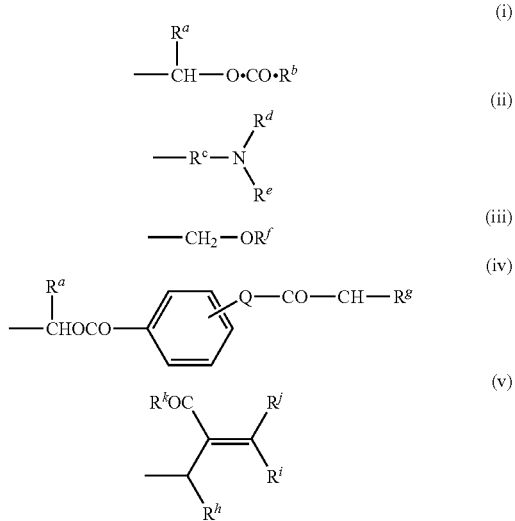

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$ cycloalkyl, 1-amino$(C_{1-6})$alkyl, or
1-$(C_{1-6}$ alkyl)amino$(C_{1-6})$ alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or
$(C_{1-6})$ alkyl; $R^i$ is hydrogen, $(C_{1-6})$ alkyl optionally substituted by halogen, $(C_{2-6})$ alkenyl, $(C_{1-6})$alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$alkoxycarbonyl; and $R^k$ represents $(C_{1-8})$alkyl, $(C_{1-8})$alkoxy, $(C_{1-6})$alkoxy $(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, acetoxyethyl, pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$ alkyl groups, such as ethoxycarbonyloxymethyl, ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-$(C_{1-6})$alkoxycarbonyl)-2-$(C_{2-6})$ alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

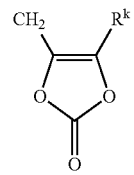

wherein $R^k$ is hydrogen, $C_{1-6}$alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such form, including pure isomeric forms. The different isomeric forms may be separated or resolved one from the other by conventional methods, or any given isomer may be obtained by conventional synthetic methods or by stereospecific or asymmetric syntheses.

One of skill in the readily appreciates that optimization for a given reaction may require some routine variation in reaction parmeters such as reaction time, temperature, energy source, pressure, light, pressure, solvent or solvents used, co-reagents, catalysts, and the like.

Protective groups wherever found herein maybe designated by their specific formula or alternatively, maybe referred to generically by P or $P_n$ (wherein n is an integer). It is to be appreciated that where generic descriptors are used, that such descriptors are at each occurrence independent from each other. Thus, a compound with more than one of the same generic descriptors (e.g. P) does not indicate that each P is the same protective group, they maybe the same or different, so long as the group is suitable to the chemistry being employed. Where protection or deprotection is generically referred to, one of ordinary skill in the art will understand this to mean that suitable conditions are employed that will allow for the removal of the protecting group to be removed while minimizing reaction at other positions of the molecule, unless otherwise indicated. Many protective groups and protective group strategies are known to those of skill in the art in maybe found in numerous references including, Greene, et al. "Protective Groups in Organic Synthesis" (Published by Wiley-Interscience), which is herein incorporated by reference in its entirety.

Leaving groups wherever found herein maybe designated by a specific chemical formula, or alternatively, maybe generically referred to as L or Ln (wherein n is an integer). It is to be appreciated that where a generic descriptor is used, that such descriptors are at each occurrence independent from each other. Leaving groups can be single atoms such as Cl, Br, or I, or maybe a group such as $OSO_2CH_3$, $OC(=O)CH_3$, $O(C=O)CF_3$, $OSO_2CF_3$, and the like. Leaving groups may be formed during the course of a reaction and thus a compound containing a leaving group may not always be an isolated material but rather as a reactive intermediate. By way of non-limiting example, a carboxylic acid maybe reacted with a coupling reagent such as DCC, CDI, EDCI, isobutyl chloroformate, etc, and the corresponding reative intermediate thus formed is further reacted with the nucleophilic coupling partner. In such cases, one of skill in the art appreciates that the activation step maybe performed before the introduction of the nucleophilic coupling partner, or in some cases, even in the presence of the nucleophilic coupling partner (depending upon the identity of the particular activating agent, carboxylic acid and nuclephilic coupling partner used). One skilled in the art readily ascertains that leaving groups generally refer to atoms or groups which can be eliminated, substituted or otherwise dissociate during the course of the reaction.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

The compounds of this invention may also be used in the manufacture of medicaments useful in treating bacterial infections in humans or other mammals.

All publications, including but not limited to patents and patent applications, cited in this specification are herein incorporated by reference (whether specifically stated to be so or not) as if each individual publication were specifically and individually indicated to be incorporated by reference herein as though fully set forth.

The following examples illustrate the preparation of certain compounds of formula (I) and the activity of certain compounds of formula (I) against various bacterial organisms. Although specific examples are described in the schemes, one of skill in the art appreciates that the methods are more generally applicable.

One of skill in the art readily appreciates that although the following schemes describe specific examples, they maybe more generally applied to produce additional embodiments of this invention. Furthermore, the examples set forth below are illustrative of the present invention and are not intended to limit, in any way, the scope of the present invention.

The compounds of the present invention were prepared by the methods illustrated in Schemes I, II and III.

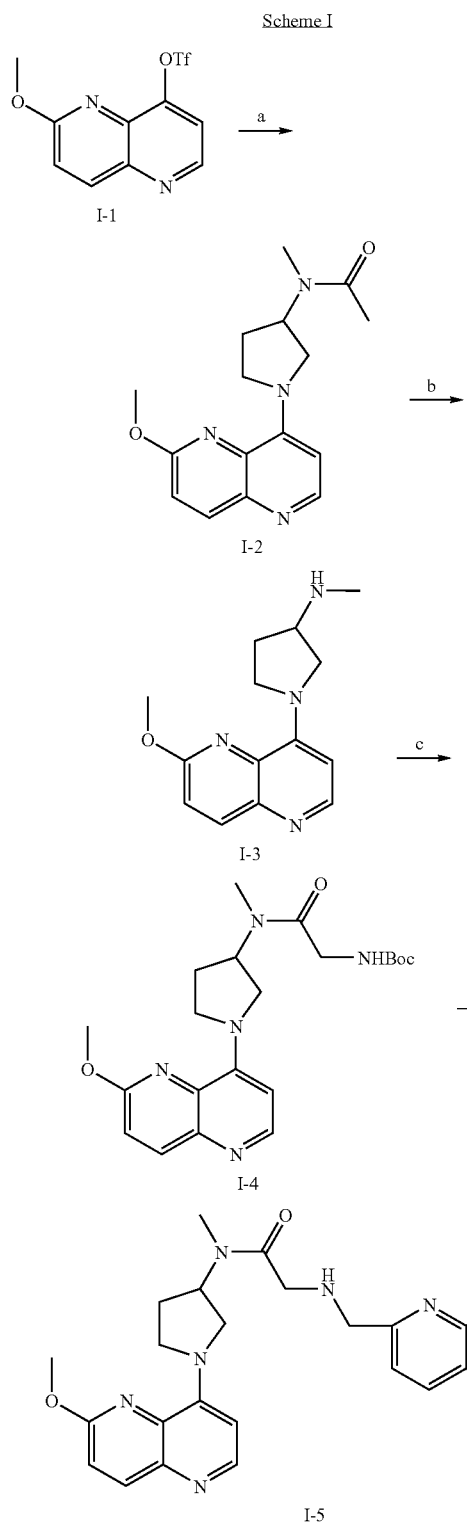

Reagents and conditions: (a) 3-(N-acetyl-N-methylamino) pyrrolidine, dioxane, TEA, 50° C. (b) 3N HCl in H₂O, reflux (c) Boc-gly-OH, PyBOP, N-methyl morpholine, 0-25° C. (d) 4N HCl in dioxane, CHCl₃; then TEA, 3-oxo-3,4-dihydro-2H-pyrido[3,2-b][1,4]oxazine-6-carbaldehyde, NaBH₄, DCM-MeOH (1:3), 25° C.

Coupling of the appropriate pyrrolidine, for example 3-(N-acetyl-N-methylamino)pyrrolidine (TCI Chemicals) as shown, into the desired coupling partner (exemplified by naphthyridine triflate (I-1)) provided adduct (I-2). Additional pyrrolidines and coupling partners maybe used to prepare further embodiments of this invention. The acetyl group was hydrolysized unmasking amine (I-3), which was then coupled with Boc-gly-OH under standard conditions affording the adduct (I-4). The Boc group was removed and the free amine was reacted with an appropriate aldehyde, for example, 3-oxo-3,4-dihydro-2H-pyrido[3,2-b][1,4]oxazine-6-carbaldehyde as shown, using standard reductive amination conditions, providing the final compound (I-5). Reaction of the free amine with additional carbaldehydes with concurrent or subsequent reduction can be used to prepare additional embodiments of this invention.

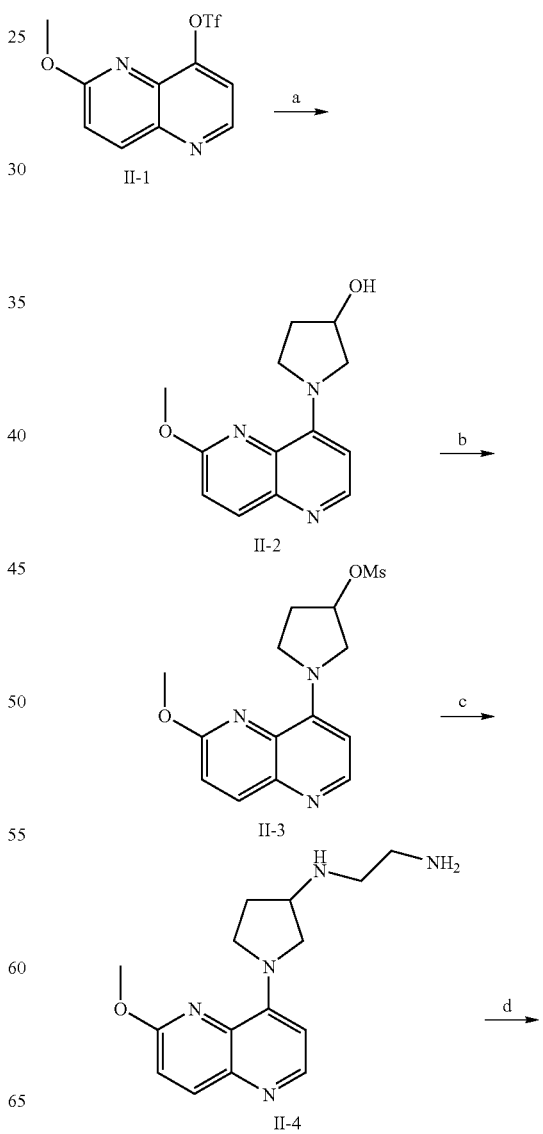

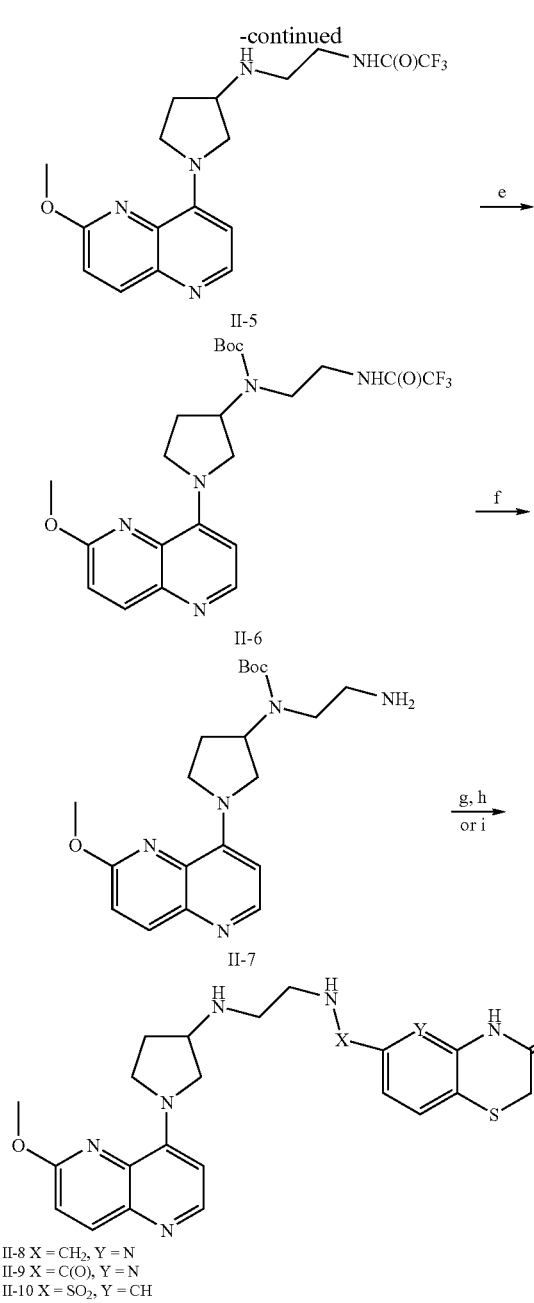

II-8 X = CH₂, Y = N
II-9 X = C(O), Y = N
II-10 X = SO₂, Y = CH

Reagents and conditions: (a) dl-3-pyrrolidinol, TEA, DMF, 25° C. (b) methanesulfonyl chloride, DMAP, DCM, 0-25° C. (c) ethylene diamine, 100° C. (d) ethyl trifluoroacetate, THF, 0° C. (e) bis(1,1-dimethylethyl) dicarbonate, THF (f) K₂CO₃, MeOH—H₂O, 25° C. (g) 3-oxo-3,4-dihydro-2H-pyrido[3,2-b][1,4]thiazine-6-carbaldehyde, DIPEA, Na₂SO₄, DCM-EtOH; then NaBH₄, 25° C. (h) 3-oxo-3,4-dihydro-2H-pyrido[3,2-b][1,4]thiazine-6-carboxylic acid, DIPEA, 1-(3-dimethylaminopropyl)-3-ethylcarbodimide, 1-hydroxyenzotriazole, DMF, 25° C.; then 4N HCl in dioxane (i) DIPEA, 3-oxo-3,4-dihydro-2H-pyrido[3,2-b][1,4]thiazine-6-sulfonyl chloride, DCM, 25° C.

Coupling of an appropriately substituted pyrrolidine (exemplified above by 3-hydroxypyrrolidine) into the desired coupling partner (exemplified by naphthyridine triflate (I-1)) afforded adduct (II-2). Additional pyrrolidines and coupling partners maybe used to prepare additional embodiments of the invention. The hydroxyl group was activated, exemplified by conversion to the mesylate (II-3) as shown above, and then displaced with the desired amine, exemplified by ethylene diamine providing amine (II-4). The hydroxyl group is also activated by other reagents and maybe replaced by different amines to render additional embodiments of this invention as desired. The resulting primary amine was protected, as exemplified using the trifluoroacetate and the remaining secondary amine protected as exemplified, as the Boc carbamate (II-6). Alternative protecting groups for the amines maybe chosen in accordance to what is known to those of skill in the art. See for example, Greene, et al, described previously herein. The trifluoroacetate group was then removed and the resulting primary amine (II-7) underwent reductive amination with an appropriate aldehyde, such as 3-oxo-3,4-dihydro-2H-pyrido[3,2-b][1,4]thiazine-6-carbaldehyde, forming (II-8) and was coupled with the appropriate acid, such as 3-oxo-3,4-dihydro-2H-pyrido[3,2-b][1,4]thiazine-6-carboxylic acid, and sulfonyl chloride, such as 3-oxo-3,4-dihydro-2H-pyrido[3,2-b][1,4]thiazine-6-sulfonyl chloride, to generate amide (II-9) and sulfonamide (II-10), respectively. Additional aldehydes, activated sulfonic acid and carboxylic acid derivatives maybe also used in order to prepare additional embodiments of this invention. Further derivativization of the compounds are also contemplated where such derivativization renders further embodiments of the present invention. By way of non-limiting example, it is possible that the non-tertiary nitrogens are selectively functionalized by additional reactions to provide further substitution on one or more of the nitrogens as in accordance with the described embodiments of this invention.

Scheme III

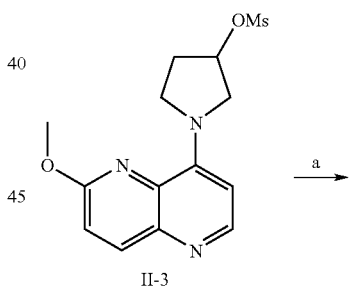

II-3

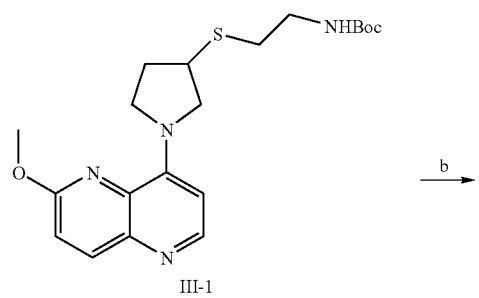

III-1

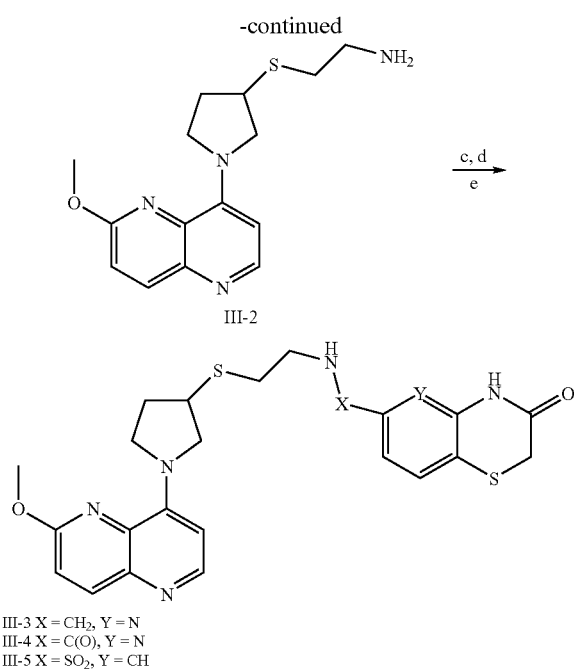

III-3 X = CH₂, Y = N
III-4 X = C(O), Y = N
III-5 X = SO₂, Y = CH

Reagents and conditions: (a) NaH, tert-butyl N-(2-mercaptoethyl) carbamate, DMF, 25° C. (b) 4N HCl in dioxane, CHCl₃ (c) 3-oxo-3,4-dihydro-2H-pyrido[3,2-b][1,4]thiazine-6-carbaldehyde, DIPEA, Na₂SO₄, DCM-EtOH; then NaBH₄, 25° C. (d) 3-oxo-3,4-dihydro-2H-pyrido[3,2-b][1,4]thiazine-6-carboxylic acid, DIPEA, 1-(3-Dimethylaminopropyl)-3-ethylcarbodimide, 1-hydroxyenzotriazole, DMF, 25° C.; then 4N HCl in dioxane (e) DIPEA, 3-oxo-3,4-dihydro-2H-pyrido[3,2-b][1,4]thiazine-6-sulfonyl chloride, DCM, 25° C.

Mesylate (II-3) (prepared as shown in scheme II) was subsequently replaced with an appropriate thiol, exemplified by tert-butyl N-(2-mercaptoethyl) carbamate to render compound III-1. Additional thiols maybe used in the substitution reaction to prepare additional embodiments of this invention. Furthermore, the thioether thus formed maybe oxidized to a sulfoxide or sulfone in accordance with certain embodiments of this invention. The Boc group was removed and the resulting primary amine (III-2) underwent reductive amination with the appropriate aldehyde, exemplified here by 3-oxo-3, 4-dihydro-2H-pyrido[3,2-b][1,4]thiazine-6-carbaldehyde forming III-3. The amine was also coupled with a desired carboxylic acid, exemplified in this case by 3-oxo-3,4-dihydro-2H-pyrido[3,2-b][1,4]thiazine-6-carboxylic acid to generate compound III-4. The amine was also reacted with an appropriate sulfonic acid derivative, in this case the sulfonyl chloride, 3-oxo-3,4-dihydro-2H-pyrido[3,2-b][1,4]thiazine-6-sulfonyl chloride to give compound III-5.

Additional aldehydes, sulfonic acid and carboxylic acid derivatives maybe also used in order to prepare additional embodiments of this invention. Further derivativization of the compounds are also contemplated where such derivativization renders further embodiments of the present invention. By way of non-limiting example, it is possible that the non-tertiary nitrogens are selectively functionalized by additional reactions to provide further substitution on one or more of the nitrogens as in accordance with the described embodiments of this invention.

General

Proton nuclear magnetic resonance (¹H NMR) spectra were recorded at 400 MHz, and chemical shifts are reported in parts per million (δ) downfield from the internal solvent standard CHCl₃ or MeOH. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl₃ is deuteriochloroform and CD₃OD is tetradeuteriomethanol. Mass spectra were obtained using electrospray (ES) ionization techniques. All temperatures are reported in degrees Celsius. E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

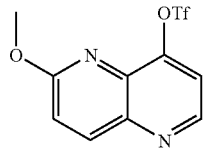

Preparation of 6-(methyloxy)-1,5-naphthyridin-4-yl trifluoromethanesulfonate (a) 4-Hydroxy-6-methoxy-[1,5]-naphthyridine 5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipitate was filtered to give the title compound (6.26 g, 70%)

(b) 6-(methyloxy)-1,5-naphthyridin-4-yl trifluoromethanesulfonate

4-Hydroxy-6-methoxy-[1,5]-naphthyridine (10 g, 0.057 mol) in DCM (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified via column chromatography (silica, dichloromethane (DCM)) to generate the title compound as an off-white solid (13.2 g, 77%): MS (APCl+) m/z 309 (M+H)$^+$.

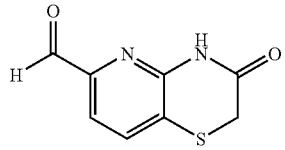

Preparation 2

Preparation of 3-Oxo-3,4-dihydro-2H-pyrido[3,2-b][1,4]thiazine-6-carboxaldehyde (a) Methyl 3-oxo-3,4-dihydro-2H-pyrido[3,2-b][1,4]thiazine-6-carboxylate A solution of ethyl 2-mercaptoacetate (1.47 mL) in DMF (48 mL) was ice-cooled and treated with sodium hydride (540 mg of a 60% dispersion in oil). After 1 h methyl 6-amino-5-bromopyridine-2-carboxylate (3 g) (T. R. Kelly and F. Lang, J. Org. Chem. 61, 1996, 4623-4633) was added and the mixture stirred for 16 h at room temperature. The solution was diluted with EtOAc (1 L), washed with water (3×300 mL), dried and evaporated to about 10 mL. The white solid was filtered off and washed with a little EtOAc to give the ester (0.95 g); LC/MS (APCl$^-$) m/z 223 ([M−H]$^-$, 100%).

(b) 3-Oxo-3,4-dihydro-2H-pyrido[3,2-b][1,4]thiazine-6-carboxylic acid

A solution of methyl 3-oxo-3,4-dihydro-2H-pyrido[3,2-b][1,4]thiazine-6-carboxylate (788 mg) in dioxane (120 ml)/water (30 mL) was treated dropwise over 2 h with 0.5M NaOH solution (8 mL) and stirred overnight. After evaporation to approx. 3 ml, water (5 mL) was added and 2M HCl to pH4. The precipitated solid was filtered off, washed with a small volume of water and dried under vacuum to give a solid (636 mg); LC/MS (APCl$^-$) m/z 209 ([M−H]$^-$, 5%), 165([M-COOH]$^-$, 100%).

(c) 6-Hydroxymethyl-3-oxo-3,4-dihydro-2H-pyrido[3,2-b][1,4]thiazine

A solution of 3-oxo-3,4-dihydro-2H-pyrido[3,2-b][1,4]thiazine-6-carboxylic acid (500 mg) in THF (24 mL) with triethylamine (0.396 mL) was cooled to −10° C. and isobutyl chloroformate (0.339 ml) was added. After 20 minutes the suspension was filtered through kieselguhr into an ice-cooled solution of sodium borohydride (272 mg) in water (8 mL), the mixture stirred 30 minutes and the pH reduced to 7 with dilute HCl. The solvent was evaporated and the residue triturated under water. The product was filtered and dried under vacuum to give a white solid (346 mg); LC/MS (APCl$^-$) m/z 195 ([M−H]$^-$, 50%), 165 (100%).

(d) 3-Oxo-3,4-dihydro-2H-pyrido[3,2-b][1,4]thiazine-6-carboxaldehyde

A solution of 6-hydroxymethyl-3-oxo-3,4-dihydro-2H-pyrido[3,2-b][1,4]thiazine (330 mg) in dichloromethane (30 mL)/THF (30 mL) was treated with manganese dioxide (730 mg) and stirred at room temperature. Further manganese dioxide was added after 1 h (730 mg) and 16 h (300 mg). After a total of 20 h the mixture was filtered through kieselguhr and the filtrate evaporated. The product was triturated with EtOAc/hexane (1:1) and collected to give a solid (180 mg); LC/MS (APCl$^-$) m/z 195 ([M−H]$^-$, 95%), 165 (100%).

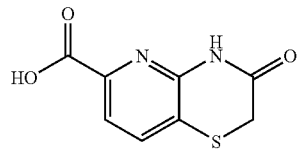

Preparation 3

Preparation of 3-oxo-3,4-dihydro-2H-pyrido[3,2-b][1,4]thiazine-6-carboxylic acid This acid was prepared from 3-oxo-3,4-dihydro-2H-pyrido[3,2-b][1,4]thiazine-6-carboxaldehyde (from Prep. 4 d) (890 mg) by oxidation with Oxone (potassium peroxymonosulphate) (3.1 g) in a DMF solution (50 mL). After 1.5 h at room temperature, dilution with water (50 mL), filtration and drying in vacuo afforded the acid as a white solid (750 mg, 77%).

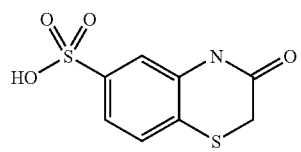

Preparation 4

Preparation of 3-oxo-3,4-dihydro-2H-1,4-benzothiazine-6-sulfonic acid

To an ice-cold solution of chlorosulfonic acid (22 mL, 33.1 mmol) was added the benzothiazinone (6 g, 36.3 mmol) portion-wise. The dark blue solution was warmed up to 25° C. over 1 h, then heated at 45° C. for 2 h. After cooling, addition of the solution to ice-water resulted in the formation of a white precipitate. The solid was filtered, washed with H$_2$O/Hexane and dried in vacuo to afford the title compound as a white solid (8.46 g, 88%); MS (APCl+) m/z 246 (M+H)$^+$.

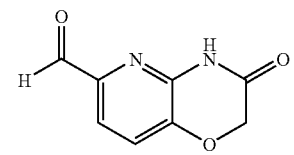

Preparation 5

Preparation of 3-Oxo-3,4-dihydro-2H-pyrido[3,2-b][1,4]oxazine-6-carboxaldehyde (a) 2-Bromo-5-hydroxy-6-nitropyridine 3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 mL). The solvent was removed in vacuo to afford material (30 g, 96%), which was used without further purification: MS (ES) m/z 219.0 (M+H)$^+$.

(b) Ethyl (6-bromo-2-nitro-pyridin-3-yloxy)acetate

2-Bromo-5-hydroxy-6-nitropyridine (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et$_2$O. The precipitate was removed by suction filtration, and the filtrate was concentrated in vacuo to afford material (38 g, 89%), which was used without further purification; MS (ES) m/z 305.0 (M+H)$^+$.

(c) 6-Bromo-4H-pyrido[3,2-b][1,4]oxazin-3-one

Ethyl (6-bromo-2-nitro-pyridin-3-yloxy)acetate (38 g, 0.125 mole) was dissolved in glacial AcOH (150 mL), and iron powder (20 g, 0.36 mole) was added. The mixture was mechanically stirred and heated at 90° C. for 5 h, then was cooled to room temperature and diluted with EtOAc (300 mL). The mixture was filtered through a pad of silica gel and the filtrate was concentrated in vacuo and the residue recrystallized from MeOH (15 g, 52%); MS (ES) m/z 229.0 (M+H)$^+$.

(d) 6-((E)-Styryl)-4H-pyrido[3,2-b][1,4]oxazin-3-one

6-Bromo-4H-pyrido[3,2-b][1,4]oxazin-3-one (6.0 g, 26.3 mmole) and trans-2-phenylvinylboronic acid (3.9 g, 26.3 mmole) were dissolved in 1,4-dioxane (150 mL) and the solution was degassed with argon. (Ph$_3$P)$_4$Pd (230 mg, 0.2 mmole) was added, followed by a solution of potassium carbonate (6.9 g, 50 mmole) in H$_2$O (20 mL). The reaction was heated at reflux under argon overnight, then was cooled to room temperature and diluted with EtOAc (200 mL). The solution was washed sequentially with H$_2$O and brine, dried (Na$_2$SO$_4$), and concentrated in vacuo. The solid residue was purified by flash chromatography on silica gel (5-10% EtOAc/CHCl$_3$) to afford a solid (2.5 g, 38%): LCMS (ES) m/z 253.0 (M+H)$^+$.

e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (1.2 g, 4.8 mmole) was dissolved in CH$_2$Cl$_2$ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with Et$_2$O (50 mL). The collected solid was washed with additional Et$_2$O and dried to afford a solid (700 mg, 82%): MS (ES) m/z 179.0 (M+H)$^+$.

Preparation 6

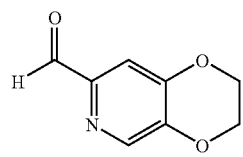

Preparation of 2,3-Dihydro-[1,4]dioxino[2,3-c]pyridine-7-carboxaldehyde (a) 5-Benzyloxy-2-hydroxymethyl-1H-pyridin-4-one A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 mL), and ethanol (20 mL) was heated to reflux overnight. The mixture was allowed to cool to room temperature then filtered. The resultant solid was washed with ether and dried in vacuo (5.9 g); MS (APCl+) m/z 232 (MH+).

(b) (2,3-Dihydro-[1,4]dioxino[2,3-c]pyridin-7-yl)-methanol

A solution of 5-benzyloxy-2-hydroxymethyl-1H-pyridin-4-one (2 g, 8.7 mmol) in water (220 mL) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 mL) then treated with potassium carbonate (2.9 g) and 1,2-dibromoethane (0.6 mL, 7 mmol). The mixture was heated at 85° C. overnight. The cooled mixture was evaporated onto silica and chromatographed eluting with 10-30% methanol in ethyl acetate affording a white solid (250 mg, 21%): MS (APCl+) m/z 168 (MH+).

(c) 2,3-Dihydro-[1,4]dioxino[2,3-c]pyridine-7-carboxaldehyde

A solution of (2,3-dihydro-[1,4]dioxino[2,3-c]pyridin-7-yl)-methanol (250 mg, 1.5 mmol) in dichloromethane (5 mL) was treated with manganese dioxide (650 mg, 7.5 mmol). After 3 days the mixture was filtered and evaporated affording a white solid (150 mg, 61%); MS (APCl+) m/z 166 (MH+).

EXAMPLE 1

Preparation of N$^1$-methyl-N$^1$-{1-[6-(methyloxy)-1,5-naphthyridin-4-yl]-3-pyrrolidinyl}-N$^2$-[(3-oxo-3,4-dihydro-2H-pyrido[3,2-b][1,4]oxazin-6-yl)methyl] glycinamide (a) N-[1-(6-Methoxy-[1,5]naphthyridin-4-yl)-pyrrolidin-3-yl]-N-methyl-acetamide

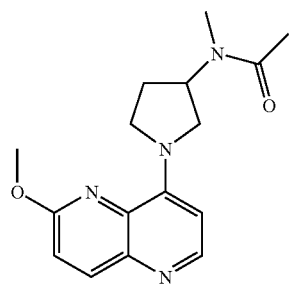

3-(N-acetyl-N-methylamino)pyrrolidine (1.00 g, 7.0 mmol) was dissolved in dioxane (15 mL) and treated with 1,1,1-Trifluoro-methanesulfonic acid 6-methoxy-[1,5]naphthyridin-4-yl ester (1.67 g, 5.4 mmol) and triethylamine (0.98 mL, 7.0 mmol). After stirring at 50° C. overnight the reaction mixture was cooled, concentrated to dryness and purified via column chromatography (silica, 2% MeOH in chloroform) to afford the title compound as an off-white solid (1.72 g, quantitive): LC-MS m/z 301 (M+H)$^+$ (b) [1-(6-Methoxy-[1,5]naphthyridin-4-yl)-pyrrolidin-3-yl]-methyl-amine

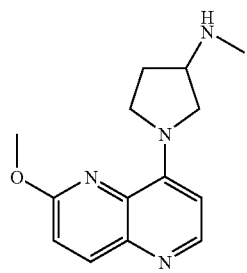

N-[1-(6-Methoxy-[1,5]naphthyridin-4-yl)-pyrrolidin-3-yl]-N-methyl-acetamide (500 mg, 1.67 mmol) was suspended in 3N HCl (aq) and refluxed overnight. The solution was evaporated to dryness and azeotroped with acetonitrile to provide the title compound (1.2 g, 85%) as a white solid: LC-MS mlz 259 (M+H)+

(c) ({[1-(6-Methoxy-[1,5]naphthyridin-4-yl)-pyrrolidin-3-yl]-methyl-carbamoyl}-methyl)-carbamic acid tert-butyl ester

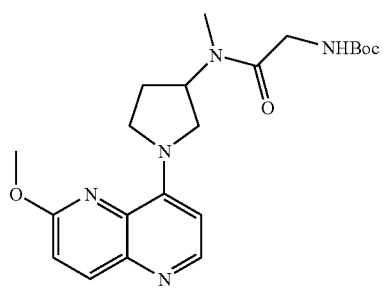

Boc-protected glycine (226 mg, 1.3 mmol) was dissolved in dichloromethane and cooled in an ice bath. [1-(6-Methoxy-[1,5]naphthyridin-4-yl)-pyrrolidin-3-yl]-methyl-amine (569 mg, 1.6 mmol) was added along with PyBOP (723 mg, 1.6 mmol) and N-methyl morpholine (0.71 mL, 6.4 mmol). The reaction mixture was stirred overnight while allowing to warm to room temperature. The resulting suspension was diluted with chloroform and washed twice with 0.5N HCl, water, saturated aqueous sodium bicarbonate solution and brine. The organic layer was dried over magnesium sulfate, filtered, concentrated and purified via column chromatography (silica, 2% MeOH in chloroform) to afford the title compound (272 mg, 42%) as a purple solid: LC-MS m/z 416 (M+H)+

(d) N$^1$-methyl-N$^1$-{1-[6-(methyloxy)-1,5-naphthyridin-4-yl]-3-pyrrolidinyl}-N$^2$-[(3-oxo-3,4-dihydro-2H-pyrido[3,2-b][1,4]oxazin-6-yl)methyl]glycinamide

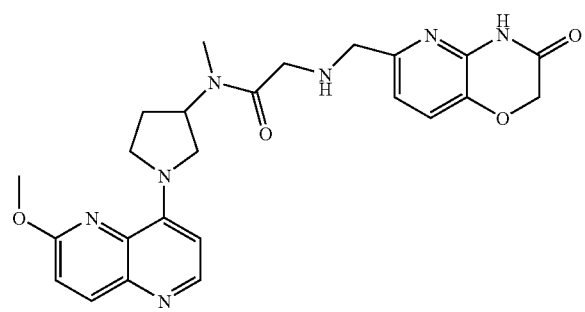

({[1-(6-Methoxy-[1,5]naphthyridin-4-yl)-pyrrolidin-3-yl]-methyl-carbamoyl}-methyl)-carbamic acid tert-butyl ester (272 mg, 0.66 mmol) was dissolved in a minimum amount of chloroform and treated with 4N HCl in dioxane (3 mL). After stirring 1 h, the reaction mixture was concentrated to dryness and azeotroped with toluene. The resulting HCl salt (302 mg, 0.66 mmol) was dissolved in methanol/dichloromethane (8 mL, 1:3) and treated with triethylamine (0.46 mL, 3.3 mmol) and 3-Oxo-3,4-dihydro-2H -pyrido[3,2-b][1,4]oxazine-6-carbaldehyde (117 mg, 0.66 mmol) and stirred for 72 hours. The solution was diluted with a small amount of methanol and treated with sodium borohydride (25 mg, 0.66 mmol.) After stirring 90 minutes, the reaction mixture was diluted with chloroform and poured into saturated aqueous sodium bicarbonate solution. The aqueous layer was extracted with chloroform. The combined organic layers were washed with brine, dried over magnesium sulfate, filtered, concentrated and chromatographed in chloroform/methanol/ammonia. The resulting solid was converted to a di-HCl salt of the title compound as an off-white solid (27 mg, 8.6%): LC-MS m/z 478 (M+H)+; $^1$H NMR (CDCl$_3$, 400 MHz) δ 8.25 (d, 1H, J=6 Hz), 8.02 (d, J=9 Hz, 1H), 7.29 (m, 1H), 7.11 (d, J=9 Hz, 1H), 6.99 (d, J=8 Hz, 1H), 6.62 (d, J=6 Hz, 1H), 5.23 (m, 1H), 4.63 (m, 2H), 4.18 (m, 3H), 4.01 (m, 3H), 3.81 (m, 2H), 3.68 (s, 1H), 3.57 (s, 1H), 3.00 (s, 2H), 2.26 (m, 2H).

EXAMPLE 2

Preparation of N-[2z-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-carboxamide (a) 1-[6-(methyloxy)-1,5-naphthyridin-4-yl]-3-pyrrolidinol

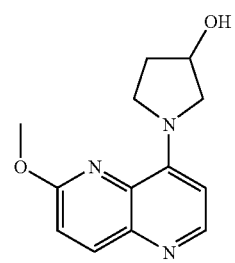

1,1,1-Trifluoro-methanesulfonic acid 6-methoxy-[1,5]naphthyridin-4-yl ester (20 g, 65 mmol) was dissolved in DMF and treated with triethylamine (12 mL, 84 mmol) and DL-3-pyrrolidinol (7.4 g , 84 mmol.) The reaction mixture was stirred overnight at room temperature. The resulting reaction mixture was diluted with water (200 mL) and stirred for 1 h. The resulting precipitate was filtered off, washed with diethyl ether, and air dried to afford the title compound: LC-MS m/z 246 (M+H)+

(b) Methanesulfonic acid 1-(6-methoxy-[1,5]naphthyridin-4-yl)-pyrrolidin-3-yl ester

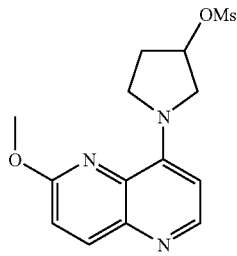

1-(6-Methoxy-[1,5]naphthyridin-4-yl)-pyrrolidin-3-ol (7.67 g, 31.3 mmole), triethylamine (8.73 mL, 63 mmole) and catalytic amount of 4-dimethylaminopyridine dissolved in DCM (100 mL) and cooled to 0° C. The solution was degassed with argon. Methanesulfonyl chloride (2.9 mL, 37.6 mmole) was added dropwise over 30 minutes. The reaction was stirred under argon for 30 minutes at 0° C. and then stirred at room temperature for 1 h. The reaction mixture was concentrated in vacuo. The residue was purified on column chromatography (silica, 1-5% MeOH in chloroform). The solvent was removed in vacuo to afford the title compound as a white solid (7.0 g, 69%): LC-MS (ES) m/z 324 $(M+H)^+$.

(c) $N^1$-[1-(6-Methoxy-[1,5]naphthyridin-4-yl)-pyrrolidin-3-yl]-ethane-1,2-diamine

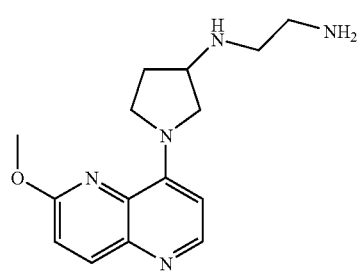

Methanesulfonic acid 1-(6-methoxy-[1,5]naphthyridin-4-yl)-pyrrolidin-3-yl ester (1.96 g, 6.1 mmol) was heated to 100° C. in ethylene diamine (10 mL, 150 mmol) overnight. The reaction mixture was cooled, diluted with water and extracted 4× with a solution of 10% isopropanol in chloroform. The combined organic layers were washed with brine, dried over magnesium sulfate, and purified by column chromatography (silica, 10% MeOH in chloroform) to afford the title coompound as a white solid (1.3 g, quantitative yield as an adduct of two moles of water): LC/MS m/z 288 $(M+H)^+$.

(d) 2,2,2-trifluoro-N-[2-({1-[6-(methyloxy)-1,5-naphthyridin-4-yl]-3-pyrrolidinyl}amino)ethyl]acetamide

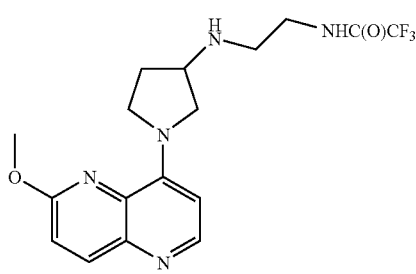

To a solution of $N^1$-[1-(6-Methoxy-[1,5]naphthyridin-4-yl)-pyrrolidin-3-yl]-ethane-1,2-diamine (1.3 g, 4.53 mmol) in THF (50 mL) at 0° C. was slowly added ethyl trifluoroacetate (1.19 mL, 4.53 mmol). The solution was stirred for 1.5 h and concentrated. The resulting solid was used without further purification (1.73 g, quantitive): LC/MS m/z 384 $(M+H)^+$.

(e) 1,1-dimethylethyl {1-[6-(methyloxy)-1,5-naphthyridin-4-yl]-3-pyrrolidinyl}{2-[(trifluoroacetyl)amino]ethyl}carbamate

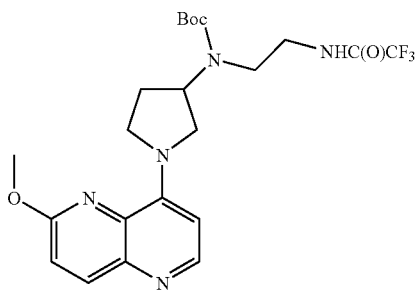

Bis(1,1-dimethylethyl) dicarbonate (870 mg, 4.9 mmol) and 2,2,2-trifluoro-N-[2-({1-[6-(methyloxy)-1,5-naphthyridin-4-yl]-3-pyrrolidinyl}amino)ethyl]acetamide (1.4 g, 3.65 mmol) were mixed in THF (50 mL) and stirred at 25° C. for 12 h. The solution was concentrated and the resulting solid was used without further purification (1.8 g, quantitative): LC-MS m/z 484 $(M+H)^+$.

(f) 1,1-dimethylethyl (2-aminoethyl){1-[6-(methyloxy)-1,5-naphthyridin-4-yl]-3-pyrrolidinyl}carbamate

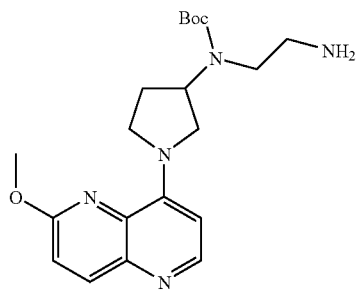

To a solution of 1,1-dimethylethyl {1-[6-(methyloxy)-1,5-naphthyridin-4-yl]-3-pyrrolidinyl}{2-[(trifluoroacetyl)amino]ethyl}carbamate (1.8 g, 3.65 mmol) in MeOH/$H_2O$ (75 mL, 2:1) was added $K_2CO_3$ (2.52 g, 18.25 mmol). After 12 h at 25° C., the reaction was concentrated under reduced pressure and purified via column chromatography [silica, 5% MeOH in DCM (2% $NH_4OH$)] affording the title compound (1.24 g, 88%) as an off-white solid: LC/MS (ES) m/e 388 $(M+H)^+$.

(g) N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-carboxamide

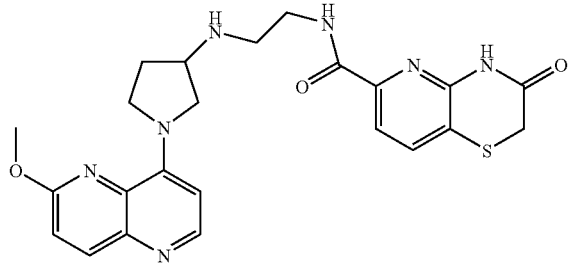

To a solution of 1,1-dimethylethyl (2-aminoethyl){1-[6-(methyloxy)-1,5-naphthyridin-4-yl]-3-pyrrolidinyl}carbamate (630 mg, 1.62 mmol) in DMF (20 mL) were added 3-oxo-3,4-dihydro-2H-pyrido[3,2-b][1,4]thiazine-6-carboxylic acid (340 mg, 1.62 mmol), 1-(3-Dimethylaminopropyl)-3-ethylcarbodimide (340 mg, 1.78 mmol) and 1-hydroxybenzotriazole (240 mg, 1.78 mmol). After 12 h at room temperature, the solution was concentrated and purified by column chromatography (silica,1% MeOH in DCM (1% NH$_4$OH)). The resulting solid was treated with HCl solution (10 mL, 4N in dioxane). The solution was concentrated to provide the HCl salt of title compound as an off-white solid (570 mg, 74%): LC/MS (ES) m/e 580 (M+H)$^+$; $^1$H NMR (CD$_3$OD, 400 MHz) δ 8.31 (d, J=6.8 Hz, 1H), 8.12 (d, J=9.2 Hz, 1H), 7.82 (d, J=7.7 Hz, 1H), 7.6 (bs, 1H), 7.37 (d, J=9.2 Hz, 1H), 6.91 (bs, 1H), 5.0-5.2 (m, 1H), 4.75 (s, 1H), 4.24 (s, 1H), 4.11 (s, 3H), 3.69-3.82 (m, 7H), 3.44-3.69 (m, 3H), 2.60-2.63 (m, 1H), 2.47 (bs, 1H).

EXAMPLE 3

Preparation of N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-sulfonamide

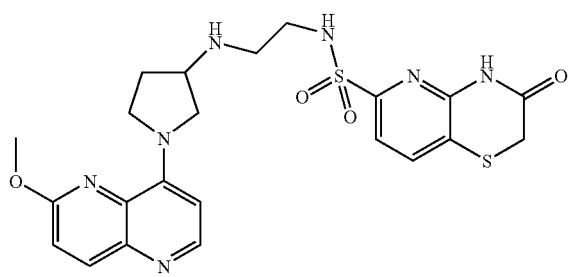

N$^1$-[1-(6-Methoxy-[1,5]naphthyridin-4-yl)-pyrrolidin-3-yl]-ethane-1,2-diamine (213 mg, 0.74 mmol) (from Example 2c) was dissolved in DCM (2 mL) with triethylamine (0.31 mL, 2.2 mmol) and cooled in an ice bath. The cooled solution was treated with 3-oxo-3,4-dihydro-2H-benzo[1,4]thiazine-6-sulfonyl chloride and stirred 45 minutes. The reaction mixture was diluted with chloroform and poured into saturated aqueous sodium bicarbonate solution. The aqueous layer was extracted with chloroform, and the combined organic layers were washed with brine, dried over magnesium sulfate, concentrated and purified by column chromatography (silica, 0-10% MeOH in CDCl$_3$ (1% NH$_4$OH) to afford the title compound as a white solid (174 mg, 46%): LC/MS m/z 515 (M+H)$^+$; $^1$H NMR (CDCl$_3$, 400 MHz) δ 8.28 (d, J=5 Hz, 1H), 8.04 (d, J=9 Hz, 1H), 7.43-7.36 (m, 2H), 6.97 (d, J=9 Hz, 1H), 6.30 (d, J=5 Hz, 1H), 4.03 (m, 1H), 3.94 (s, 3H), 3.85 (m, 1H), 3.71 (m, 1H), 3.43 (s, 2H), 3.38 (m, 1H), 3.06 (m, 2H), 2.82 (m, 2H), 2.10 (m, 1H), 1.85 (m, 1H), 1.70-1.60 (m, 1H).

This material, as a solution in MeOH, was treated with an excess of 4M HCl in dioxane and evaporated to dryness to provide the dihydrochloride salt of the title compound.

EXAMPLE 4

Preparation of 6-({2-[1-(6-Methoxy-[1,5]naphthyridin-4-yl)-pyrrolidin-3-ylamino]-ethylamino}-methyl)-4H-pyrido[3,2-b][1,4]oxazin-3-one dihydrochloride

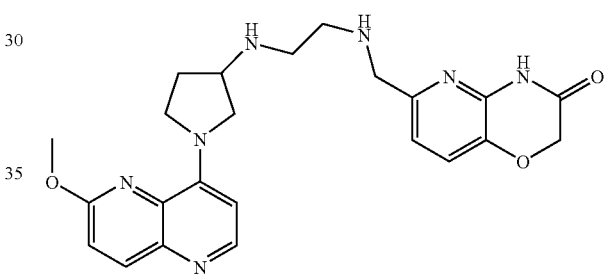

N$^1$-[1-(6-Methoxy-[1,5]naphthyridin-4-yl)-pyrrolidin-3-yl]-ethane-1,2-diamine (250 mg, 0.77 mmol) (from Example 2c) was dissolved in MeOH:DCM (8 mL, 1:1) and treated with 3-oxo-3,4-dihydro-2H-pyrido[3,2-b][1,4]oxazine-6-carbaldehyde (138 mg, 0.77 mmol). After stirring overnight, the reaction mixture was treated with sodium borohydride (29 mg, 0.77 mmol) and stirred 1 h. The reaction mixture was diluted with chloroform and poured into saturated aqueous sodium bicarbonate solution. The aqueous layer was extracted several times with chloroform. The combined organic layers were washed with brine, dried over magnesium sulfate, filtered, concentrated to dryness and purified by colume chromatography (silica, 0-10% MeOH in CDCl$_3$ (1% NH$_4$OH)) to afford the title compound as a white solid (140 mg, 40%): LC/MS m/z 450 (M+H)$^+$; $^1$H NMR (CDCl$_3$, 400 MHz) δ 8.34 (d, J=5 Hz, 1H), 8.07 (d, J=9 Hz, 1H), 7.17 (d, J=8 Hz, 1H), 7.01 (d, J=9 Hz, 1H), 6.88 (d, J=8 Hz, 1H), 6.40 (d, J=5 Hz, 1H), 4.62 (s, 2H), 4.15 (m, 1H), 4.05 (m, 1H), 3.99 (s, 3H), 3.95 (m, 1H), 3.77 (s, 3H), 3.47 (m, 1H), 2.82 (m, 2H), 2.80 (s, 2H), 2.20 (m, 1H), 1.92 (m, 1H).

This material, as a solution in MeOH, was treated with an excess of 4M HCl in dioxane and evaporated to dryness to provide the dihydrochloride salt of the title compound.

EXAMPLE 5

Preparation of 6-({2-[1-(6-Methoxy-[1,5]naphthyridin-4-yl)-pyrrolidin-3-ylamino]-ethylamino}-methyl)-4H-pyrido[3,2-b][1,4]thiazin-3-one dihydrochloride

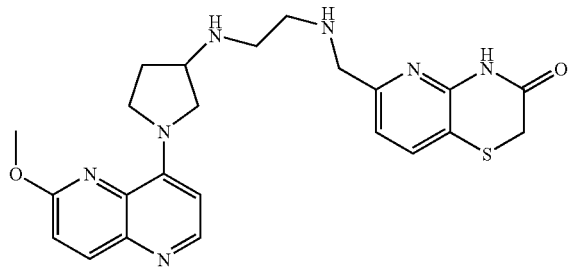

The title compound (209 mg, 58%) as a green solid was prepared according to Example 4, excepting substituting 3-oxo-3,4-dihydro-2H-pyrido[3,2-b ][1,4]thiazine-6-carbaldehyde (250 mg, 0.77 mmol) for 3-oxo-3,4-dihydro-2H-pyrido[3,2-b][1,4]oxazine-6-carbaldehyde: LC/MS m/z 466 (M+H)$^+$; $^1$H NMR (CDCl$_3$, 400 MHz) δ 8.34 (d, 1H, J=5 Hz), 8.07 (d, J=9 Hz, 1H), 7.54 (d, J=8 Hz, 1H), 7.01 (d, J=9 Hz, 1H), 6.93 (d, J=8 Hz, 1H), 6.41 (d, J=6 Hz, 1H), 4.15 (m, 1H), 4.05 (m, 1H), 3.99 (s, 3H), 3.95 (m, 1H), 3.80 (s, 3H), 3.48 (m, 1H), 3.46 (s, 2H), 2.83 (m, 2H), 2.80 (s, 2H), 2.20 (m, 1H), 1.92 (m, 1H).

This material, as a solution in MeOH, was treated with an excess of 4M HCl in dioxane and evaporated to dryness to provide the dihydrochloride salt of the title compound.

EXAMPLE 6

Preparation of N-(2,3-Dihydro-[1,4]dioxino[2,3-c]pyridin-7-ylmethyl)-N'-[1-(6-methoxy-[1,5]naphthyridin-4-yl) -pyrrolidin-3-yl]-ethane-1,2-diamine dihydrochloride

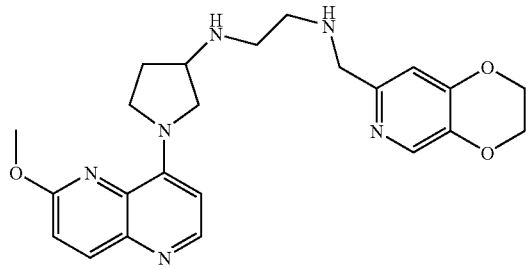

The title compound (180 mg, 53%) as a white solid was prepared according to Example 4, excepting substituting 2,3-dihydro[1,4]dioxino[2,3-c]pyridine-7-carbaldehyde (128 mg, 0.77 mmol) for 3-oxo-3,4-dihydro-2H-pyrido[3,2-b ][1,4]oxazine-6-carbaldehyde: LC/MS m/z 437 (M+H)$^+$; $^1$H NMR (CDCl$_3$, 400 MHz) δ 8.34 (d, 1H, J=5 Hz), 8.10 (s, 1H), 8.06 (d, J=9 Hz, 1H), 7.00 (d, J=9 Hz, 1H), 6.80 (s, 1H), 6.42 (d, J=6 Hz, 1H), 4.31 (m, 1H), 4.27 (m, 1H), 4.20 (bs, 1H), 4.00 (s, 3H), 3.95 (m, 1H), 3.78 (s, 3H), 3.46 (m, 1H), 2.80 (m, 4H), 2.21 (m, 1H), 1.88 (m, 1H).

This material, as a solution in MeOH, was treated with an excess of 4M HCl in dioxane and evaporated to dryness to provide the dihydrochloride salt of the title compound.

EXAMPLE 7

Preparation of 6-({[2-({1-[6-(methyloxy)-1.5-naphthyridin-4-yl]-3-Pyrrolidinyl}thio)ethyl]amino}methyl)-2H-pyrido[3.2-b][1,4]thiazin-3(4H)-one (a) 1,1-dimethylethyl [2-({1-[6-(methyloxy)-1,5-naphthyridin-4-yl]-3-pyrrolidinyl}thio)ethyl]carbamate

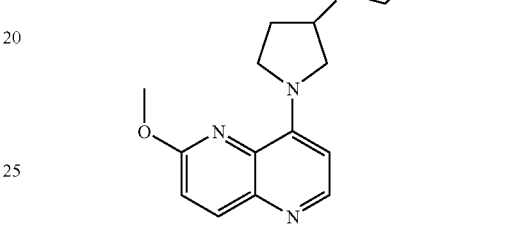

To a solution of methanesulfonic acid 1-(6-methoxy-[1,5]naphthyridin-4-yl)-pyrrolidin-3-yl ester (650 mg, 2 mmol, prepared as Example 2b) in DMF (3 mL) was added NaH (89 mg, 2.2 mmol, 65% in mineral oil) followed by 1,1-dimethylethyl (2-mercaptoethyl)carbamate (0.373 mL, 2.2 mmol). The resulting mixture was stirred at 25° C. for 12 h and then diluted with brine. Chloroform was used the extracted the aqueous solution. The organic fractions were pooled, concentrated and purified with column chromatography (silica, 10% MeOH in CDCl$_3$ (1% NH$_4$OH)) to afford the title compound as an off-white solid (630 mg, 78%): LC/MS m/z 405 (M+H)$^+$.

(b) 6-({[2-({1-[6-(methyloxy)-1,5-naphthyridin-4-yl]-3-pyrrolidinyl}thio)ethyl]amino}methyl)-2H-pyrido[3,2-b][1,4]thiazin-3(4H)-one

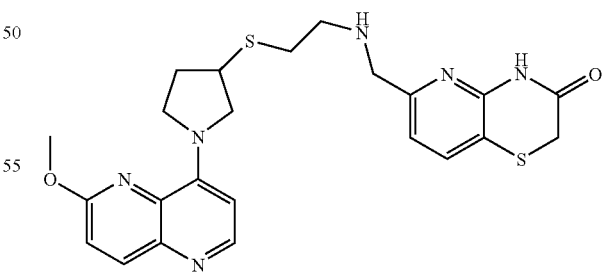

1,1-dimethylethyl [2-({1-[6-(methyloxy)-1,5-naphthyridin-4-yl]-3-pyrrolidinyl}thio)ethyl]carbamate (210 mg, 0.52 mmol) was dissolved in a minimum amount of chloroform and treated with 4N HCl in dioxane (2 mL). After stirring 2 h, the reaction mixture was concentrated to dryness and azeotroped with toluene. The resulting HCl salt of the free amine was dissolved in methanol/dichloromethane (4 mL, 1:3) and treated with triethylamine (0.36 mL, 2.6 mmol) and 3-oxo-3,4-dihydro-2H-pyrido[3,2-b][1,4]thiazine-6-carbaldehyde (101 mg, 0.52 mmol) and stirred for 12 hours. The solution was diluted with a small amount of methanol and treated with sodium borohydride (19 mg, 0.52 mmol.) After stirring 90 minutes, the reaction mixture was diluted with chloroform and poured into saturated aqueous sodium bicarbonate solution. The aqueous layer was extracted with chloroform. The combined organic layers were washed with brine, dried over magnesium sulfate, filtered, concentrated and chromatographed in chloroform/methanol/ammonia. The resulting solid was converted to an HCl salt of the title compound as a yellow solid (85 mg, 34%): LC-MS m/z 483 (M+H)$^+$; $^1$H NMR (CDCl$_3$, 400 MHz) δ 8.27-8.31 (m, 1H), 8.18-8.22 (m, 1H), 7.82-7.86 (m, 1H), 7.35-7.41 (m, 1H), 7.16-7.19 (m, 1H), 6.89-6.94 (m, 1H), 7.39-7.42 (m, 2H), 4.2-4.27 (m, 1H), 4.14 (s, 3H), 3.84-3.98 (m, 3H), 3.69-3.75 (m, 1H), 3.55 (s, 2H), 3.42-3.50 (m, 2H), 3.16-3.26 (m, 2H), 2.55-2.63 (m, 1H), 2.18-2.22 (m, 1H).

EXAMPLE 8

Preparation of 6-({[2-({1-[6-(methyloxy)-1.5-naphthyridin-4-yl]-3-Pyrrolidinyl}thio)ethyl]amino}methyl)-2H-Pyrido[3,2-b][1,4]oxazin-3(4H)-one

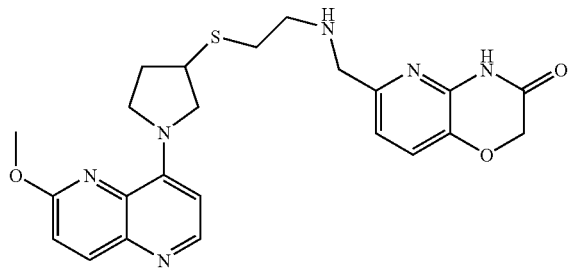

The title compound (110 mg, 47%) as a light yellow solid was prepared according to Example 7, excepting substituting 3-oxo-3,4-dihydro-2H-pyrido[3,2-b][1,4]oxazine-6-carbaldehyde (88 mg, 0.5 mmol) for 3-oxo-3,4-dihydro-2H-pyrido[3,2-b][1,4]thiazine-6-carbaldehyde: LC/MS m/z 467 (M+H)$^+$; $^1$H NMR (CDCl$_3$, 400 MHz) δ 8.39 (d, J=5.7 Hz, 1H), 8.27 (d, J=9.0 Hz, 1H), 7.25 (d, J=8.1 Hz, 1H), 7.10 (d, J=9.1 Hz, 1H), 6.99 (d, J=8.1 Hz, 1H), 6.49 (d, J=5.8 Hz, 1H), 4.69 (s, 2H), 4.50-4.59 (m, 1H), 4.08-4.22 (m, 6H), 3.95 (s, 2H), 3.68-3.70 (m, 1H), 3.0-3.03 (m, 2H), 2.95-2.98 (m, 2H), 2.48-2.57 (m, 1H), 2.19-2.28 (m, 1H).

This material, as a solution in MeOH, was treated with an excess of 4M HCl in dioxane and evaporated to dryness to provide the hydrochloride salt of the title compound.

EXAMPLE 9

Preparation of N-(2,3-dihydro[1,4]dioxino[2,3-c]pyridin-7-ylmethyl)-2-({1-[6-(methyloxy)-1,5-naphthyridin-4-yl]-3-pyrrolidinyl}thio)ethanamine

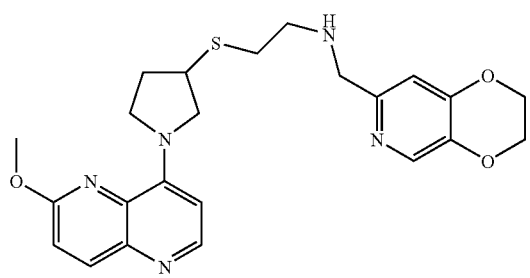

The title compound (120 mg, 51%) as a light yellow solid was prepared according to Example 7, excepting substituting 2,3-dihydro[1,4]dioxino[2,3-c]pyridine-7-carbaldehyde (86 mg, 0.52 mmol) for 3-oxo-3,4-dihydro-2H-pyrido[3,2-b][1,4]thiazine-6-carbaldehyde: LC/MS m/z 454 (M+H)$^+$; $^1$H NMR (CDCl$_3$, 400 MHz) δ 8.36 (d, J=4.4 Hz, 2H), 8.14 (d, J=9.0 Hz, 1H), 8.10 (s, 1H), 7.29 (s, 1H), 7.08 (d, J=9.0 Hz, 1H), 6.85 (s, 1H), 6.44 (d, J=4.4 Hz, 1H), 4.43-4.48 (m, 1H), 4.35-4.38(m, 2H), 4.30-4.34 (m, 2H), 3.95-4.10 (m, 6H), 3.84 (s, 2H), 2.91-2.94 (m, 2H), 2.83-2.86 (m, 2H), 2.56-2.64 (br, 1H), 2.39-2.42 (m, 1H), 2.06-2.11 (m, 1H).

This material, as a solution in MeOH, was treated with an excess of 4M HCl in dioxane and evaporated to dryness to provide the hydrochloride salt of the title compound.

EXAMPLE 10

Preparation of N-[2-({1-[6-(methyloxy)-1,5-naphthyridin-4-yl]-3-pyrrolidinyl}thio)ethyl]-3-oxo-3,4-dihydro-2H-pyrido[3,2-b][1,4]thiazine-6-carboxamide

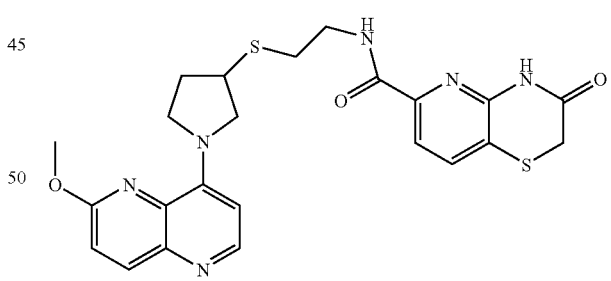

The hydrochloride salt of [2-({1-[6-(methyloxy)-1,5-naphthyridin-4-yl]-3-pyrrolidinyl}thio)ethyl]amine (from Example 7b) (300 mg, 0.88 mmol) was dissolved in DCM (5 mL) with triethylamine (0.31 mL, 2.2 mmol) and cooled in an ice bath. The cooled solution was treated with ethyl chloroformate (0.15 mL, 1.59 mmol) and triethyl amine (0.79 mL, 5.3 mmol) and stirred for 1 h. 3-oxo-3,4-dihydro-2H-pyrido[3,2-b][1,4]thiazine-6-carboxylic acid (222 mg, 1.06 mmol) was added. After stirring at 25° C. for 12 h, the reaction mixture was diluted with chloroform and poured into saturated aqueous sodium bicarbonate solution. The aqueous layer was extracted with chloroform, and the combined organic layers were washed with brine, dried over magnesium sulfate, concentrated and purified by column chromatography (silica, 0-10% MeOH in CDCl₃ (1% NH₄OH) to afford the title compound as a white solid (170 mg, 39%): LC/MS m/z 497 (M+H)⁺; ¹H NMR (CDCl₃, 400 MHz) δ 8.33 (d, J=4.4 Hz, 1H), 8.29 (br, 1H), 8.2 (d, J=9.0 Hz, 1H), 8.02-8.06 (m, 1H), 7.88 (d, J=7.8 Hz, 1H), 7.81 (d, J=7.8 Hz, 1H), 7.09 (d, J=9.0 Hz, 1H), 6.47 (d, J=4.4 Hz, 1H), 4.47-4.49 (m, 1H), 3.95-4.15 (m, 6H), 3.75-3.81 (m, 2H), 3.64-3.70 (m, 2H), 3.13-3.17 (m, 1H), 2.92-2.94 (m, 2H), 2.47-2.52 (m, 1H), 2.11-2.19 (m, 1H).

This material, as a solution in MeOH, was treated with an excess of 4M HCl in dioxane and evaporated to dryness to provide the dihydrochloride salt of the title compound.

EXAMPLE 11

Preparation of N-[2-({1-[6-(methyloxy)-1,5-naphthyridin-4-yl]-3-pyrrolidinyl}thio)ethyl]-3-oxo-3,4-dihydro-2H-1,4-benzothiazine-6-sulfonamide

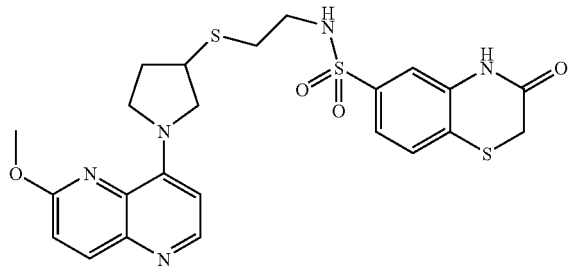

To the solution of HCl salt of [2-({1-[6-(methyloxy)-1,5-naphthyridin-4-yl]-3-pyrrolidinyl}thio)ethyl]amine (from Example 7b) (420 mg, 1.23 mmol) in DCM/MeOH (15 mL, 1:1) with triethylamine (0.86 mL, 6.1 mmol) was added 3-oxo-3,4-dihydro-2H-1,4-benzothiazine-6-sulfonyl chloride (388 mg, 1.48 mmol). After stirring at 25° C. for 12 h, the reaction mixture was diluted with chloroform and poured into saturated aqueous sodium bicarbonate solution. The aqueous layer was extracted with chloroform, and the combined organic layers were washed with brine, dried over magnesium sulfate, concentrated and purified by column chromatography (silica, 0-10% MeOH in CDCl₃ (1% NH₄OH) to afford the title compound as a white solid (400 mg, 61%): LC/MS m/z 532 (M+H)⁺; ¹H NMR (CDCl₃, 400 MHz) δ 9.05. (br, 1H), 8.34 (d, J=5.8 Hz, 1H), 8.23 (d, J=9.0 Hz, 1H), 7.57 (s, 1H), 7.55 (d, J=7.4 Hz, 1H), 7.48 (d, J=8.1 Hz, 1H), 7.07 (d, J=9.0 Hz, 1H), 6.45 (d, J=5.9 Hz, 1H), 6.2 (br, 1H), 4.38-4.43 (m, 1H), 3.93-4.18 (m, 6H), 3.52-3.61 (m, 1H), 3.47 (s, 2H), 3.22-3.28 (m, 2H), 2.82-02.87 (m, 2H), 2.4-2.47 (m, 1H), 1.99-2.08 (m, 1H).

This material, as a solution in MeOH, was treated with an excess of 4M HCl in dioxane and evaporated to dryness to provide the dihydrochloride salt of the title compound.

EXAMPLE 12

Preparation of N-[2-({1-[6-(methyloxy)-1,5-naphthyridin-4-yl]-3-pyrrolidinyl}thio)ethyl]-2,3-dihydro-1,4-benzodioxin-6-sulfonamide

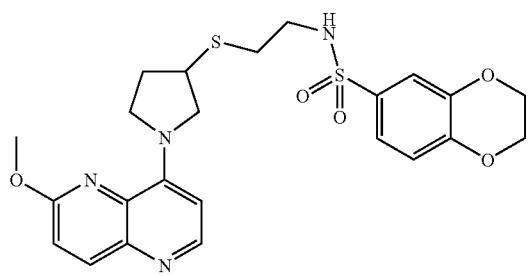

The title compound (95 mg, 36%) as a white solid was prepared according to Example 11, excepting substituting 2,3-dihydro-1,4-benzodioxin-6-sulfonyl chloride (128 mg, 0.77 mmol) for 3-oxo-3,4-dihydro-2H-1,4-benzothiazine-6-sulfonyl chloride: LC/MS m/z 503 (M+H)⁺; ¹H NMR (CDCl₃, 400 MHz) δ 8.34 (d, J=5.6 Hz, 1H), 8.17 (d, J=9.0 Hz, 1H), 7.41 (s, 1H), 7.38 (d, J=8.5 Hz, 1H), 7.05 (d, J=9.0 Hz, 1H), 6.96 (d, J=8.5 Hz, 1H), 6.43 (d, J=5.7 Hz, 1H), 5.24-5.31 (m, 1H), 4.4-4.46 (m, 1H), 4.31-4.38 (m, 4H), 4.07-4.11 (m, 1H), 4.02 (s, 3H), 3.96-4.0 (m, 2H), 3.5-3.53 (m, 1H), 3.24-3.29 (m, 2H), 2.82-2.86 (m, 2H), 2.38-2.42 (m, 1H), 2.01-2.04 (m, 1H).

This material, as a solution in MeOH, was treated with an excess of 4M HCl in dioxane and evaporated to dryness to provide the hydrochloride salt of the title compound.

EXAMPLE 13

Preparation of N-[2-({1-[6-(methyloxy)-1,5-naphthyridin-4-yl]-3-pyrrolidinyl}sulfonyl)ethyl]-3-oxo-3,4-dihydro-2H-1,4-benzothiazine-6-sulfonamide (a) 1,1-dimethylethyl [2-({1-[6-(methyloxy)-1,5-naphthyridin-4-yl]-3-pyrrolidinyl}sulfonyl)ethyl]carbamate

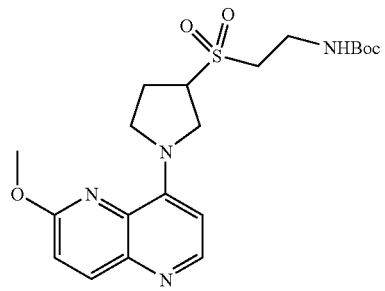

1,1-dimethylethyl [2-({1-[6-(methyloxy)-1,5-naphthyridin-4-yl]-3-pyrrolidinyl}thio)ethyl]carbamate (250 mg, 0.62 mmol, from Example 7a) and oxone (1014 g, 1.86 mmol) was mixed in THF/H₂O (8 mL, 3:1) and stirred at 25° C. for 12 h. The resulting solution was partitioned between ethyl acetate and water. The aqueous layer was extracted several times with ethyl acetate. The organic frations were combined, concentrated and purified with column chromatography (silica, 5-10% MeOH in CHCl₃) to afford the title compound as an off-white solid (150 mg, 55%): LC/MS m/z 437 (M+H)⁺.

(b) [2-({1-[6-(methyloxy)-1,5-naphthyridin-4-yl]-3-pyrrolidinyl}sulfonyl)ethyl]amine

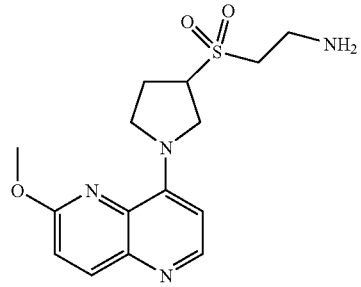

1,1-dimethylethyl [2-({1-[6-(methyloxy)-1,5-naphthyridin-4-yl]-3-pyrrolidinyl}sulfonyl)ethyl]carbamate (150 mg, 0.34 mmol) was dissolved in a minimum amount of chloroform and treated with 4N HCl in dioxane (2 mL). After stirring 2 h, the reaction mixture was concentrated to dryness and azeotroped with toluene to afford HCl salt of the title compound as a yellow solid which was used without further purification (100 mg, 88%): LC/MS m/z 337 (M+H)⁺.

(c) N-[2-({1-[6-(methyloxy)-1,5-naphthyridin-4-yl]-3-pyrrolidinyl}sulfonyl)ethyl]-3-oxo-3,4-dihydro-2H-1,4-benzothiazine-6-sulfonamide (GSK193173)

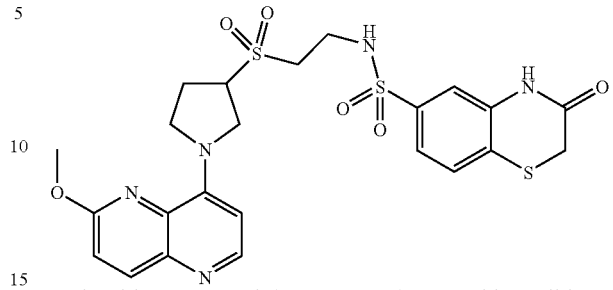

The title compound (35 mg, 30%) as a white solid was prepared according to example 11, except substituting [2-({1-[6-(methyloxy)-1,5-naphthyridin-4-yl]-3-pyrrolidinyl}sulfonyl)ethyl]amine (78 mg, 0.21 mmol) for [2-({1-[6-(methyloxy)-1,5-naphthyridin-4-yl]-3-pyrrolidinyl}thio)ethyl]amine: LC/MS m/z 564 (M+H)⁺; ¹H NMR (CD₃OD, 400 MHz) δ 8.33 (d, J=5.0 Hz, 1H), 8.08 (d, J=9.0 Hz, 1H), 7.57 (d, J=8.1 Hz, 1H), 7.41 (s, 1H), 7.36 (d, J=8.2 Hz, 1H), 7.16 (d, J=9.0 Hz, 1H), 6.63 (d, J=5.4 Hz, 1H), 5.49-5.52 (m, 1H), 5.31-5.36 (m, 1H), 5.2-5.25 (m, 1H), 3.96 (s, 4H), 3.84-3.91 (m, 1H), 3.6 (s, 2H), 3.42-3.48 (m, 2H), 3.22-3.28 (m, 2H), 2.43-2.48 (m, 2H).

This material, as a solution in MeOH, was treated with an excess of 4M HCl in and evaporated to dryness to provide the dihydrochloride salt of the title compound.

| Example | Structure | Formula |
|---|---|---|
| 1 | 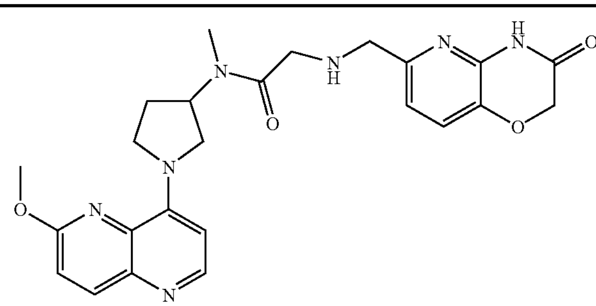 | N¹-methyl-N¹-{1-[6-(methyloxy)-1,5-naphthyridin-4-yl]-3-pyrrolidinyl}-N²-[(3-oxo-3,4-dihydro-2H-pyrido[3,2-b][1,4]oxazin-6-yl)methyl]glycinamide |
| 2 | 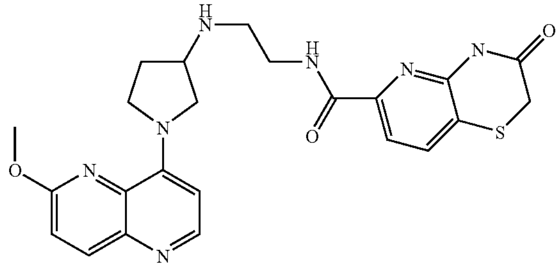 | N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-carboxamide |

| Example | Structure | Formula |
|---|---|---|
| 3 | 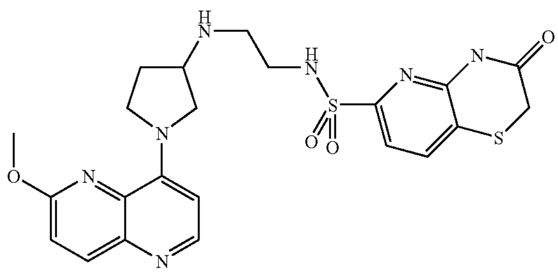 | N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-sulfonamide |
| 4 | 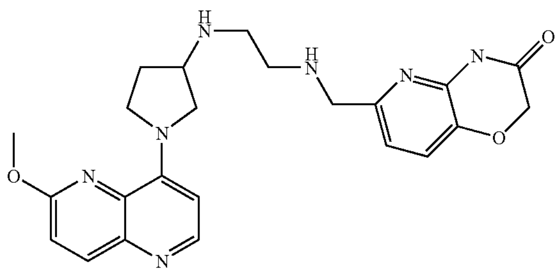 | 6-({[2-({1-[6-(methyloxy)-1,5-naphthyridin-4-yl]-3-pyrrolidinyl}amino)ethyl]amino}methyl)-2H-pyrido[3,2-b][1,4]oxazin-3(4H)-one |
| 5 | 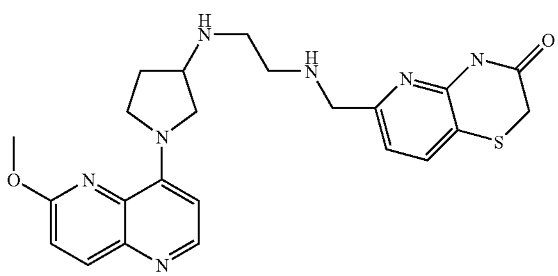 | 6-({[2-({1-[6-(methyloxy)-1,5-naphthyridin-4-yl]-3-pyrrolidinyl}amino)ethyl]amino}methyl)-2H-pyrido[3,2-b][1,4]thiazin-3(4H)-one |
| 6 | 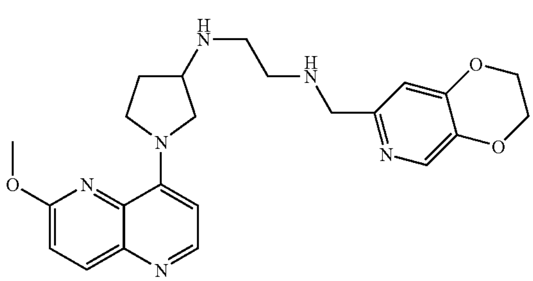 | N-(2,3-dihydro[1,4]dioxino[2,3-c]pyridin-7-ylmethyl)-N'-{1-[6-(methyloxy)-1,5-naphthyridin-4-yl]-3-pyrrolidinyl}-1,2-ethanediamine |
| 7 | 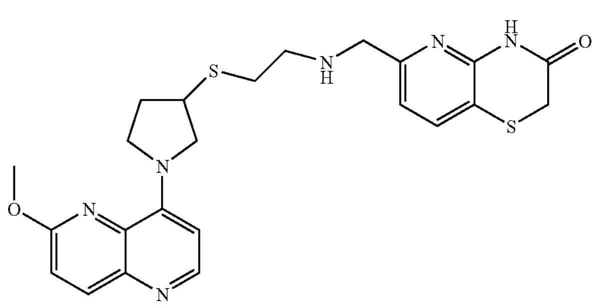 | 6-({[2-({1-[6-(methyloxy)-1,5-naphthyridin-4-yl]-3-pyrrolidinyl}thio)ethyl]amino}methyl)-2H-pyrido[3,2-b][1,4]thiazin-3(4H)-one |

-continued

| Example | Structure | Formula |
|---|---|---|
| 8 | 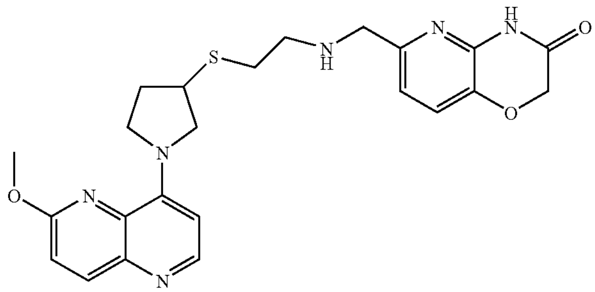 | 6-({[2-({1-[6-(methyloxy)-1,5-naphthyridin-4-yl]-3-pyrrolidinyl}thio)ethyl]amino}methyl)-2H-pyrido[3,2-b][1,4]oxazin-3(4H)-one |
| 9 | 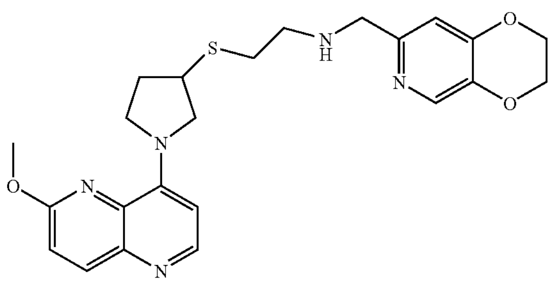 | (2,3-dihydro[1,4]dioxino[2,3-c]pyridin-7-ylmethyl)[2-({1-[6-(methyloxy)-1,5-naphthyridin-4-yl]-3-pyrrolidinyl}thio)ethyl]amine |
| 10 | 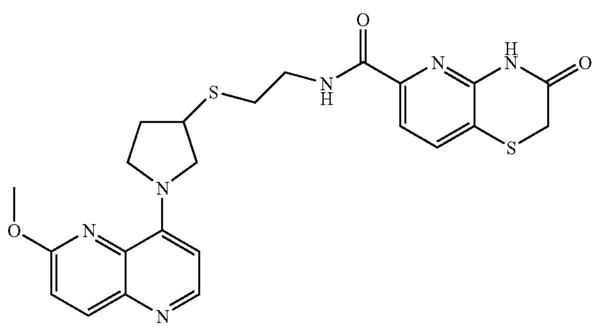 | N-[2-({1-[6-(methyloxy)-1,5-naphthyridin-4-yl]-3-pyrrolidinyl}thio)ethyl]-3-oxo-3,4-dihydro-2H-pyrido[3,2-b][1,4]thiazine-6-carboxamide |
| 11 | 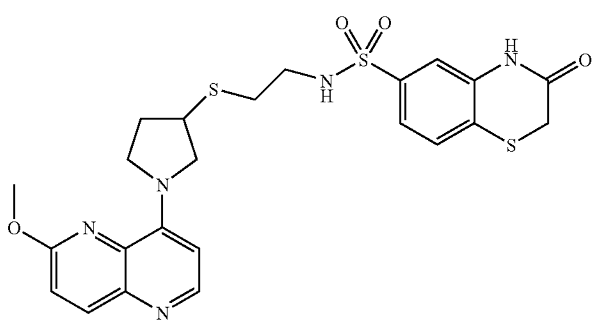 | N-[2-({1-[6-(methyloxy)-1,5-naphthyridin-4-yl]-3-pyrrolidinyl}thio)ethyl]-3-oxo-3,4-dihydro-2H-1,4-benzothiazine-6-sulfonamide |
| 12 | 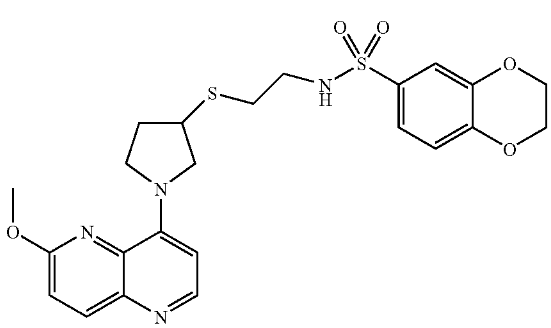 | N-[2-({1-[6-(methyloxy)-1,5-naphthyridin-4-yl]-3-pyrrolidinyl}thio)ethyl]-2,3-dihydro-1,4-benzodioxin-6-sulfonamide |

| Example | Structure | Formula |
|---|---|---|
| 13 | 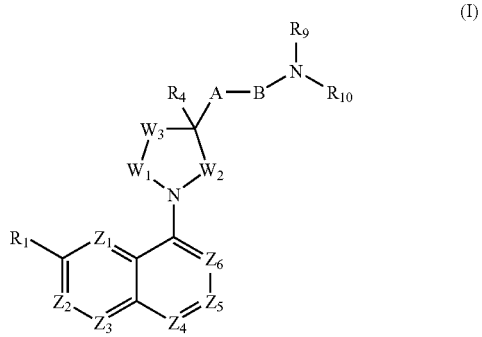 | N-[2-({1-[6-(methyloxy)-1,5-naphthyridin-4-yl]-3-pyrrolidinyl}sulfonyl)ethyl]-3-oxo-3,4-dihydro-2H-1,4-benzothiazine-6-sulfonamide |

EXAMPLE 14

Antimicrobial Activity Assay

Whole-cell antimicrobial activity was determined by broth microdilution using the National Committee for Clinical Laboratory Standards (NCCLS) recommended procedure, Document M7-A6, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes*, and *Enterococcus faecalis*.

In addition, compounds were evaluated against a panel of Gram-negative strains including *Haemophilus influenzae, Moraxella catarrhalis* and *Escherichia coli*.

The minimum inhibitory concentration (MIC) was determined as the lowest concentration of compound that inhibited visible growth. A mirror reader was used to assist in determining the MIC endpoint.

One skilled in the art would consider any compound with a MIC of less than 20 mg/mL to be a potential lead compound. For instance, each of the listed Examples (1 to 7), as identified in the present application, had a MIC ≦20 mg/ml against at least one of the organisms listed above.

What is claimed is:

1. A compound of formula (I)

(I)

or a pharmaceutically acceptable salt thereof, wherein:
$Z_1$ and $Z_4$ are N;
$Z_2, Z_3, Z_5$, and $Z_6$ are each CH;
$R_1$ is $(C_{1-6})$alkoxy;
$W_1, W_2$, and $W_3$ are each $CR_2R_3$;
A is; NH, $S(O)_n$; or $NR_6(C=O)$;
B is $(CR_7R_8)_n'$;
$R_2, R_3, R_4, R_7$, and $R_8$ are each hydrogen;
$R_6$ and $R_9$ are independently hydrogen, $(C_{1-6})$alkyl;
n is 0, 1, or 2;
n' is 1 or 2;
$R_{10}$ is $UR_{11}$;
U is $CH_2$; $C(=O)$; or $SO_2$; and
$R_{11}$ is a heterocyclic ring system selected from the group consisting of
4H-Pyrido[3,2-b][1,4]thiazin-3-oxo-6-yl;
2,3-Dihydro-benzo[1,4]dioxin-6-yl;
4H-Pyrido[3,2-b][1,4]oxazin-3-oxo-6-yl; and
2,3-Dihydro-[1,4]dioxino[2,3-c]-pyridin-6-yl.

2. A compound or salt according to claim 1, wherein A is $S(O)_n$.

3. A compound or salt according to claim 1, wherein A is NH.

4. A compound or salt according to claim 1, wherein A is $NR_6(C=O)$.

5. A compound or salt according to claim 1, wherein U is $C(=O)$.

6. A compound or salt according to claim 1, wherein U is $SO_2$.

7. A compound or salt according to claim 1, wherein U is $CH_2$.

8. A compound or a pharmaceutically acceptable salt thereof, wherein the compound is selected from the group consisting of:
a) N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-sulfonamide;
b) N-[2-({1-[6-(methyloxy)-1,5-naphthyridin-4-yl]-3-pyrrolidinyl}amino)ethyl]-3-oxo-3,4-dihydro-2H-pyrido[3,2-b][1,4]thiazine-6-carboxamide;
c) 6-({[2-({1-[6-(methyloxy)-1,5-naphthyridin-4-yl]-3-pyrrolidinyl}amino)ethyl]amino}methyl)-2H-pyrido[3,2-b][1,4]oxazin-3(4H)-one;
d) 6-({[2-({1-[6-(methyloxy)-1,5-naphthyridin-4-yl]-3-pyrrolidinyl}amino)ethyl]amino}methyl)-2H-pyrido[3,2-b][1,4]thiazin-3(4H)-one;
e) N-(2,3-dihydro[1,4]dioxino[2,3-c]pyridin-7-ylmethyl)-N'-{1-[6-(methyloxy)-1,5-naphthyridin-4-yl]-3-pyrrolidinyl}-1,2-ethanediamine;

f) $N^1$-methyl-$N^1$-{1-[6-(methyloxy)-1,5-naphthyridin-4-yl]-3-pyrrolidinyl}-$N^2$-[(3-oxo-3,4-dihydro-2H-pyrido[3,2-b][1,4]oxazin-6-yl)methyl]glycinamide;

g) 6-({[2-({1-[6-(methyloxy)-1,5-naphthyridin-4-yl]-3-pyrrolidinyl}thio)ethyl]amino}methyl)-2H-pyrido[3,2-b][1,4]oxazin-3(4H)-one;

h) 6-({[2-({1-[6-(methyloxy)-1,5-naphthyridin-4-yl]-3-pyrrolidinyl}thio)ethyl]amino}methyl)-2H-pyrido[3,2-b][1,4]thiazin-3(4H)-one;

i) (2,3-dihydro[1,4]dioxino[2,3-c]pyridin-7-ylmethyl)[2-({1-[6-(methyloxy)-1,5-naphthyridin-4-yl]-3-pyrrolidinyl}thio)ethyl]amine;

j) N-[2-({1-[6-(methyloxy)-1,5-naphthyridin-4-yl]-3-pyrrolidinyl}thio)ethyl]-3-oxo-3,4-dihydro-2H-1,4-benzothiazine-6-sulfonamide;

k) N-[2-({1-[6-(methyloxy)-1,5-naphthyridin-4-yl]-3-pyrrolidinyl}sulfonyl)ethyl]-3-oxo-3,4-dihydro-2H-1,4-benzothiazine-6-sulfonamide;

l) N-[2-({1-[6-(methyloxy)-1,5-naphthyridin-4-yl]-3-pyrrolidinyl}thio)ethyl]-2,3-dihydro-1,4-benzodioxin-6-sulfonamide; and m) N-[2-({1-[6-(methyloxy)-1,5-naphthyridin-4-yl]-3-pyrrolidinyl}thio)ethyl]-3-oxo-3,4-dihydro-2H-pyrido[3,2-b][1,4]thiazine-6-carboxamide.

9. A pharmaceutical composition comprising a compound or salt according to claim 1 and a pharmaceutically acceptable carrier.

10. A method of treating Gram-positive and Gram-negative bacterial infections in mammals which comprises administering to a mammal in need thereof an effective amount of a compound or salt according to claim 1.

* * * * *